United States Patent [19]

Lang et al.

[11] Patent Number: 5,852,046

[45] Date of Patent: Dec. 22, 1998

[54] BENZO-FUSED HETEROCYCLIC COMPOUNDS HAVING A 5-MEMBERED RING PROCESSES FOR THEIR PREPARATION THEIR USE AS MEDICAMENTS THEIR USE AS DIAGNOSTIC AGENTS AND MEDICAMENTS CONTAINING THEM

[75] Inventors: Hans-Jochen Lang, Hofheim/Ts; Andreas Weichert, Egelsbach; Jan-Robert Schwark, Frankfurt am Main; Wolfgang Scholz, Eschborn; Udo Albus, Florstadt; Peter Crause, Offenbach, all of Germany

[73] Assignee: Hoechst Aktiengesellschaft, Frankfurt am Main, Germany

[21] Appl. No.: 872,180

[22] Filed: Jun. 10, 1997

Related U.S. Application Data

[63] Continuation of Ser. No. 459,661, Jun. 2, 1995, abandoned, which is a continuation-in-part of Ser. No. 282,506, Aug. 1, 1994, abandoned.

[30] Foreign Application Priority Data

Aug. 3, 1993 [DE] Germany ............... 43 26 005.5
Apr. 25, 1994 [DE] Germany ............... 44 14 316.8

[51] Int. Cl.$^6$ .................. A61K 31/40; C07D 209/10
[52] U.S. Cl. .................. 514/419; 548/491; 548/492
[58] Field of Search .................. 548/491, 492; 514/419

[56] References Cited

U.S. PATENT DOCUMENTS

| | | | |
|---|---|---|---|
| 3,780,027 | 12/1973 | Cragoe et al. ............... | 260/239.6 |
| 4,814,345 | 3/1989 | Ohlendorf et al. ........... | 514/418 |
| 5,091,394 | 2/1992 | Englert et al. ................ | 514/331 |
| 5,292,755 | 3/1994 | Englert et al. ................ | 514/331 |

FOREIGN PATENT DOCUMENTS

| | | |
|---|---|---|
| A2115755 | 3/1993 | Canada ............ 514/331 |
| A-0116360 | 8/1984 | European Pat. Off. ... 514/418 |
| A-0416499 | 3/1991 | European Pat. Off. ... 514/331 |
| A-0622356 | 11/1994 | European Pat. Off. . |
| WO 84/00875 | 3/1984 | WIPO . |
| 9606095 | 2/1996 | WIPO . |

OTHER PUBLICATIONS

Scholz et al., "Na$^+$/H$^+$ Exchange and its Inhibition in Cardiac Ischemia and Reperfusion," Basic Res. Cardiol., 88:443–455 (1993).
Scholz et al., "Hoe 694, a New Na$^+$/H$^+$ Exchange Inhibitor and its Effects in Cardiac Ischaemia," Br. J. Pharmacol., 109:562–568 (1993).
Hendrikx et al., "New Na$^+$/H$^+$ Exchange Inhibitor HOE 694 Improves Postischemic Function and High–Energy Phospate Resynthesis and Reduces Ca$^{2+}$ Overload in Isolated Perfused Rabbit Heart," Circulation, 89(6):2787–2798 (1994).

L'Allemain et al., "Blockade of the Na$^+$/H$^+$ Antiport Abolishes Growth Factor–Induced DNA Synthesis in Fibroblasts," J. Biol. Chem., 259(7):4313–4319 (1984).
Ghigo et al., "Evidence for a Role of the Na$^+$/H$^+$ Exchanger in the Colony–Stimulating–Factor–Induced Ornithine Decarboxylase Activity and Proliferation of the Human Cell Line M–07e," J. Cell. Physiol., 145:147–154(1990).
Lyons et al., "Enhancement of Hyperthermia Effect in Vivo by Amiloride and DIDS," Int. J. Radiation Oncology Biol. Phys., 25:95–103 (1992).

(List continued on next page.)

*Primary Examiner*—Joseph K. McKane
*Attorney, Agent, or Firm*—Finnegan, Henderson, Farabow, Garrett & Dunner, L.L.P.

[57] ABSTRACT

Benzo-fused heterocyclic compounds having a 5-membered ring, processes for their preperation, their use as medicaments, their use as diagnostic agents and medicaments containing them.

Benzo-fused heterocyclic compounds having a 5-membered ring, of the formula I

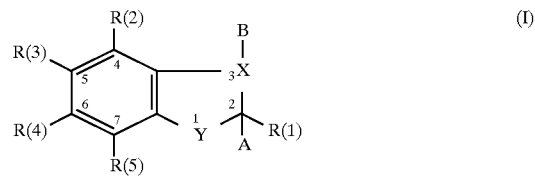

(I)

where X is N or CR(6); Y is oxygen, S or NR(7); A and B together are a bond or are both hydrogen, if, at the same time, X is CR(6) and Y is NR(7),
one of the substituents R(1) to R(6) is a —CO—N=C(NH$_2$)$_2$ group;
the other respective substituents R(1) to R(6) are H, Hal or alkyl;
up to two of the other substituents R(1) to R(6) are CN, NO$_2$, N$_3$, (C$_1$–C$_4$)-alkoxy, CF$_3$; up to one of the other substituents is R(8)—C$_n$H$_{2n}$—Z— or phenyl;
R(7) is H, alk(en)yl or R(8)—C$_n$H$_{2n}$—, and pharmaceutically tolerated salts there of, are described.

A process f or the preparation of the compounds I which comprises reacting a compound of the formula II

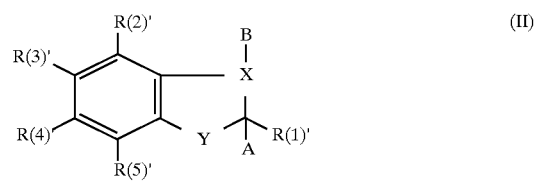

(II)

in which one of the substituents R(1)' to R(5)' is a —CO—L group and L is a leaving group which can easily be replaced nucleophilically, with guanidine, and, if appropriate, converting the product into the pharmacologically tolerated salt, furthermore is also described.

21 Claims, No Drawings

OTHER PUBLICATIONS

Maidorn et al., "Therapeutic Potential of Analogues of Amiloride: Inhibition of the Regulation of Intracellular pH as a Possible Mechanism of Tumour Selective Therapy," Br. J. Cancer, 67:297–303 (1993).

Ng et al., "Leucocyte $Na^+/H^+$ Antiport Activity in Type 1 (Insulin–Dependent) Diabetic Patients With Nephropathy," Diabetologia, 33:371–377 (1990).

Song et al., "Thermosensitization by Lowering Intracellular pH with 5–(N–ethyl–N–isopropyl) Amiloride," Radiotherapy and Oncology, 27:252–258 (1993).

BENZO-FUSED HETEROCYCLIC COMPOUNDS HAVING A 5-MEMBERED RING PROCESSES FOR THEIR PREPARATION THEIR USE AS MEDICAMENTS THEIR USE AS DIAGNOSTIC AGENTS AND MEDICAMENTS CONTAINING THEM

This application is a continuation of prior application Ser. No. 08/459,661 filed Jun. 2, 1995, now abandoned, which in turn is a continuation-in-part application of application Ser. No. 08/282.506 filed on Aug. 1, 1994, abandoned.

Benzo-fused heterocyclic compounds having a 5-membered ring, processes for their preperation, their use as medicaments, their use as diagnostic agents and medicaments containing them.

The invention relates to benzo-fused heterocyclic compounds having a 5-membered ring, of the formula I

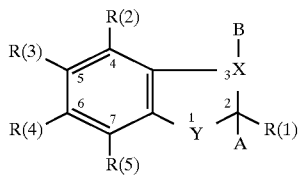 (I)

in which:

X is N or CR(6),

Y is oxygen, S or NR(7),

A and B together are a bond or are both hydrogen, if, at the same time, X is CR(6) and Y is NR (7), one of the substituents R(1) to R(6) is a —CO—N=C(NH$_2$)$_2$ group, the other respective substituents R(1) to R(6) are hydrogen, F, Cl, Br, I or (C$_1$–C$_6$)-alkyl, up to two of the other substituents R(1) to R(6) are CN, NO$_2$, N$_3$, (C$_1$–C$_4$)-alkoxy or CF$_3$, up to one of the other substituents is R(8)—C$_n$H$_{2n}$—Z—, n is zero to 10, wherein the alkylene chain —C$_n$H$_{2n}$— is straight-chain or branched and wherein a carbon atom can be replaced by an oxygen or S atom or by an N atom, R(8) is hydrogen, (C$_2$–C$_6$)-alkenyl, (C$_3$–C$_{10}$)-cycloalkyl, which is unsubstituted or substituted by 1 to 4 methyl groups or an OH group, or can contain an ethylene group —CH=CH—, and wherein a methylene group can be replaced by an oxygen or S atom or by an N atom, phenyl, which is unsubstituted or substituted by 1 to 3 substituents from the group consisting of F, Cl, Br, I, CF$_3$, CH$_3$—S(O)$_s$—, s is zero, 1 or 2, R(9)—W$_y$—, R(9) is H, methyl or ethyl, w is oxygen or NR(10), R(10) is H or methyl, y is zero or 1, C$_m$F$_{2m+1}$, m is 1 to 3, 1- or 2-naphthyl, pyridyl, quinolyl or isoquinolyl, Z is —CO—, —CH$_2$—, —[CR(11)(OH)]$_q$— q is 1, 2 or 3,

R(11) is H or methyl, oxygen, —NR(12)—,

R(12) is H or methyl,

—S(O)$_s$—, s is zero, 1 or 2,

SO$_2$—NR(13)—,

R(13) is H or (C$_1$–C$_4$)-alkyl,

R(7) is hydrogen, (C$_1$–C$_{10}$)-alkyl, (C$_2$–C$_{10}$)-alkenyl or R(8)—C$_n$H$_{2n}$—, and pharmaceutically tolerated salts thereof.

If substituents R(1) to R(5) contain one or more centers of asymmetry, the invention relates to both compounds of the S and of the R configuration. The compounds can exist as optical isomers, as racemates or as mixtures thereof.

The alkyl radicals defined can be either straight-chain or branched.

Preferred compounds of the formula I are those in which:

X is CR(6) or N,

Y is NR(7),

A and B together are a bond or are both hydrogen, if, at the same time, X is CR(6) and Y is NR(7), and the radicals R(1) to R(7) have the meaning given.

Particularly preferred compounds of the formula I are those in which:

x is CR(6) or N,

Y is NR(7),

A and B together are a bond or are both hydrogen, if, at the same time, X is CR(6) and Y is NR(7), one of the substituents R(1) to R(6) is a —CO—N=C(NH$_2$)$_2$ group, and the other respective substituents R(1) to R(6) are hydrogen, F, Cl, Br, I or (C$_1$–C$_6$)-alkyl, up to two of the other substituents R(1) to R(6) are CF$_3$ or (C$_1$–C$_4$)-alkoxy, up to one of the other substituents R(1) to R(6) is CN, NO$_2$, N$_3$ or R(8)—C$_n$H$_{2n}$—Z—, n is zero to 4, wherein the alkylene chain —C$_n$H$_{2n}$— can be straight-chain or branched and a carbon atom can be replaced by an oxygen or S atom or by an N atom, R(8) is hydrogen, (C$_3$–C$_6$)-alkenyl, (C$_5$–C$_8$)-cycloalkyl, which is unsubstituted or substituted by 1–2 methyl groups or an OH group, and wherein a methylene group can be replaced by an oxygen or S atom or by an N atom, phenyl, which is unsubstituted or substituted by 1 to 3 substituents from the group consisting of F, Cl, Br, I, CF$_3$, CH$_3$—S(O)$_s$— s is zero, 1 or 2,

R(9)—W$_y$—

R(9) is H, methyl or ethyl,

W is oxygen or NR(10),

R(10) is H or methyl, y is zero or 1,

C$_m$F$_{2m+1}$, m is 1 to 3, pyridyl, quinolyl or isoquinolyl,

Z is —CO—, —CH$_2$—, oxygen, —NR(12)—,

R(12) is H or methyl,

—S(O)$_s$—, s is zero, 1 or 2,

—SO$_2$—NR(13)—,
R(13) is H or (C$_1$–C$_4$)-alkyl,
R(7) is hydrogen, (C$_1$–C$_6$)-alkyl, (C$_2$–C$_4$)-alkenyl or R(8)—C$_n$H$_{2n}$—.

Compounds of the formula I which are preferred in particular are those in which:
X is CR(6),
Y is NR(7),
A and B together are a bond or
  are both hydrogen, if, at the same time, X is CR(6) and Y is NR(7), and
R(1) is —CO—N=C(NH$_2$)$_2$
and the other respective substituents R(2) to R(6) are
hydrogen, F, Cl or Br,
up to two of the substituents R(2) to R(6) are
  CF$_3$ or (C$_1$–C$_2$)-alkoxy,
up to one of the substituents R(2) to R(6) is
  R(8)—C$_n$H$_{2n}$—Z—,
  n is zero, 1 or 2,
    wherein the alkylene chain —C$_n$H$_{2n}$— is straight-chain or branched and
    wherein a carbon atom can be replaced by an oxygen or S atom or by an N atom,
  R(8) is hydrogen, phenyl,
    which is unsubstituted or substituted by 1 to 3 substituents from the group consisting of F, Cl, CF$_3$, CH$_3$—S(O)$_s$—,
    s is zero or 2,
    R(9)—W$_y$—,
      R(9) is H or methyl,
      W is oxygen,
      y is zero or 1,
    pyridyl, quinolyl or isoquinolyl,
  Z is —CO—, —CH$_2$—, —S(O)$_s$— or oxygen,
  s is zero, 1 or 2, and
R(7) is (C$_1$–C$_6$)-alkyl, (C$_3$–C$_4$)-alkenyl or R(8)—C$_n$H$_{2n}$—.

Especially preferred compounds are
5-chloro-1-methyl-2-indolylcarbonyl-guanidine hydrochloride,
5-chloro-1-ethyl-2-indolylcarbonyl-guanidine hydrochloride,
3-chloro-1-methyl-2-indolylcarbonyl-guanidine hydrochloride,
3,5-dichloro-1-methyl-2-indolylcarbonyl-guanidine hydrochloride,
5-fluoro-1-methyl-2-indolylcarbonyl-guanidine hydrochloride,
3-chloro-5-fluoro-1-methyl-2-indolylcarbonyl-guanidine hydrochloride,
4,6-dichloro-1,3-dimethyl-2-indolylcarbonyl-guanidine hydrochloride,
2-phenoxy-1-phenylindole-3-carboxylic acid guanidide methanesulfonic acid salt,
2-chloro-1-phenylindole-3-carboxylic acid guanidide methanesulfonic acid salt,
1-methylindoline-2-carboxylic acid guanidide hydrochloride,
5-fluoro-1-methylindoline-2-carboxylic acid guanidide hydrochloride.

Compounds of the formula I which are likewise preferred are those in which:
X is N or CR(6);
Y is oxygen, S or NR(7);
A and B together are a bond; or
A and B are both hydrogen, if, at the same time, X is CR(6) and Y is NR (7);

one of the substituents R(1) to R(5) is
  —CO—N=C(NH$_2$)$_2$; and the other respective substituents R(1) to R(5) are
hydrogen, F, Cl, Br, I or (C$_1$–C$_6$)-alkyl;
or up to two of the other respective substituents R(1) to R(5) are
CN, NO$_2$, N$_3$, (C$_1$–C$_4$)-alkyloxy or CF$_3$;
or up to one of the other respective substituents R(1) to R(5) is
R(8)—C$_n$H$_{2n}$—Z—;
n is zero to 10,
  wherein the alkylene chain —C$_n$H$_{2n}$— is straight-chain or branched and
  wherein a carbon atom can be replaced by an oxygen or S atom or by an N atom;
R(8) is hydrogen, (C$_2$–C$_6$)-alkenyl or (C$_3$–C$_{10}$)-cycloalkyl,
  which is unsubstituted or substituted by 1 to 4 methyl groups or an OH group, or can contain an ethylene group —CH=CH—, and wherein a methylene group can be replaced by an oxygen or S atom or by an N atom; or
R(8) is 1- or 2-naphthyl, pyridyl, quinolyl, isoquinolyl or phenyl,
  unsubstituted or substituted by 1 to 3 substituents chosen from the group consisting of F, Cl, Br, I, CF$_3$, CH$_3$—S(O)$_s$— and R(9)—W$_y$—;
  s is zero, 1 or 2;
  R(9) is H, methyl or ethyl;
  w is oxygen or NR(10);
  R(10) is H or methyl;
  y is zero or 1; or
R(8) is C$_m$F$_{2m+1}$;
m is 1 to 3;
Z is —CO—, —CH$_2$—, —[CR(11)(OH)]$_q$—, oxygen, —NR(12)-, —S(O)$_s$— or —SO$_2$—NR(13)-;
q is 1, 2 or 3;
R(11) is H or methyl;
R(12) is H or methyl;
s is zero, 1 or 2;
R(13) is H or (C$_1$–C$_4$)-alkyl;
R(7) is hydrogen, (C$_1$–C$_{10}$)-alkyl, (C$_2$–C$_{10}$)-alkenyl or R(8)—C$_n$H$_{2n}$—;
n is zero, 1, 2, 3 or 4;
R(8) is NR(14)R(15) or CF$_3$;
R(14) and R(15) are
  hydrogen or methyl;
R(6) is defined as R(1) to R(5),
  but with the exception of hydrogen; or
R(6) is also hydrogen,
  if one or two of the substituents R(1) to R(5) are CF$_3$; or
R(6) is also hydrogen,
  if one of the substituents R(1) to R(5) is R(8)—C$_n$H$_{2n}$—Z—;
  n is zero to 10;
    wherein the alkylene chain —C$_n$H$_{2n}$— is straight-chain or branched and wherein a carbon atom can be replaced by an oxygen or S atom or by an N atom;
  R(8) is hydrogen, (C$_2$–C$_6$)-alkenyl or (C$_3$–C$_{10}$)-cycloalkyl, which is unsubstituted or substituted by 1 to 4 methyl groups or an OH group, or can contain an ethylene group —CH=CH—, and wherein a methylene group can be replaced by an oxygen or S atom or by an N atom; or R(8) is 1- or 2-naphthyl, pyridyl, quinolyl, isoquinolyl or phenyl, unsubstituted or substituted by 1 to 3 substituents chosen from the group consisting of F, Cl, Br, I, $CF_3$, $CH_3-S(O)s-$ or $R(9)-W_y-$;
s is zero, 1 or 2;
R(9) is H, methyl or ethyl;
W is oxygen or NR(10);
R(10) is H or methyl;
y is zero or 1; or
R(8) is $C_mF_{2m+1}$;
m is 1 to 3;
Z is CO, $[CR(11)OH]_q$, $S(O)_s$ or $SO_2NR(13)$;
s is zero, 1 or 2;
q is 1, 2 or 3;
R(13) is H or $(C_1-C_4)$-alkyl; or
R(6) is also hydrogen,
if one of the substituents R(1) to R(5) is $R(8)-C_nH_{2n}-Z-$;
wherein a methylene group in the $-C_nH_{2n}-$ group is replaced by an oxygen or S atom or by an N atom;
R(8) is hydrogen, $(C_2-C_6)$-alkenyl or $(C_3-C_{10})$-cycloalkyl,
which is unsubstituted or substituted by 1 to 4 methyl groups or an OH group, or can contain an ethylene group $-CH=CH-$;
n is 1–10; or
R(6) is also hydrogen,
if one of the substituents R(1) to R(5) is $R(8)-C_nH_{2n}-Z-$;
n is zero;
R(8) is 1- or 2-naphthyl, pyridyl, quinolyl, isoquinolyl or phenyl,
unsubstituted or substituted by 1 to 3 substituents chosen from the group consisting of F, Cl, Br, I, $CF_3$, $CH_3-S(O)_s-$ or $R(9)-W_y-$;
s is zero, 1 or 2;
R(9) is H, methyl or ethyl;
W is oxygen or NR(10);
R(10) is H or methyl;
y is zero or 1;
Z is oxygen or NR(12);
R(12) is H or methyl; or
R(6) is also hydrogen,
if one of the substituents R(1) to R(5) is $R(8)C_nH_{2n}-Z$;
n is zero or 1;
R(8) is $C_mF_{2m+1}$;
m is 1 to 3;
Z is oxygen or NR(12);
R(12) is H or methyl;
and pharmaceutically tolerated salts thereof.

Compounds of the formula I which are likewise particularly preferred are those in which:
X is N or CR(6);
Y is NR(7);
A and B together are a bond or
both are hydrogen, if, at the same time, X is CR(6) and Y is NR(7)
and the radicals R(1) to R(7) are defined as above;
and pharmaceutically tolerated salts thereof.

Compounds I which are likewise especially preferred are those in which:
X is N or CR(6);
Y is NR(7);
A and B together are a bond or
A and B are both hydrogen, if, at the same time, X is CR(6) and Y is NR(7),
one of the substituents R(1) to R(5) is
$-CO-N=C(NH_2)_2$;
the other respective substituents R(1) to R(5) are
hydrogen, F, Cl, Br, I or $(C_1-C_6)$-alkyl;
or up to two of the other respective substituents R(1) to R(5) are
$(C_1-C_4)$-alkyloxy or $CF_3$;
or up to one of the other respective substituents R(1) to R(5) is
CN, $NO_2$, $N_3$ or $R(8)-C_nH_{2n}-Z-$;
n is zero to 7;
wherein the alkylene chain $-C_nH_{2n}-$ is straight-chain or branched and
wherein a carbon atom can be replaced by an oxygen or S atom or by an N atom;
R(8) is hydrogen, $(C_3-C_6)$-alkenyl or $(C_5-C_8)$-cycloalkyl,
which is unsubstituted or substituted by 1 or 2 methyl groups or an OH group, and wherein a methylene group can be replaced by an oxygen or S atom or by an N atom, or
R(8) is pyridyl, quinolyl, isoquinolyl or phenyl,
unsubstituted or substituted by 1 to 3 substituents chosen from the group consisting of
F, Cl, Br, I, $CF_3$, $CH_3-S(O)_s-$ or
$R(9)-W_y-$;
s is zero, 1 or 2;
R(9) is H, methyl or ethyl;
w is oxygen or NR(10);
R(10) is H or methyl;
y is zero or 1; or
R(8) is $C_mF_{2m+1}$;
m is 1 to 3;
Z is $-CO-$, $-CH_2-$, oxygen, $-NR(12)-$, $-S(O)_s-$ or $-SO_2-NR(13)-$;
R(12) is H or methyl;
s is zero, 1 or 2;
R(13) is H or $(C_1-C_4)$-alkyl;
R(6) is defined as R(1) to R(5),
but with the exception of hydrogen; or
R(6) is also hydrogen,
if one or two of the substituents R(1) to R(5) are $CF_3$; or
R(6) is also hydrogen,
if one of the substituents R(1) to R(5) is $R(8)-C_nH_{2n}-Z-$;
n is zero to 4;
wherein the alkylene chain $-C_nH_{2n}-$ is straight-chain or branched and wherein a carbon atom can be replaced by an oxygen or S atom or by an N atom; or
R(8) is hydrogen, $(C_3-C_6)$-alkenyl or $(C_5-C_8)$-cycloalkyl,
which is unsubstituted or substituted by 1 or 2 methyl groups or an OH group, and wherein a methylene group can be replaced by an oxygen or S atom or by an N atom; or
R(8) is pyridyl, quinolyl or isoquinolyl or phenyl,
unsubstituted or substituted by 1 to 3 substituents chosen from the group consisting of
F, Cl, Br, I, $CF_3$, $CH_3-S(O)_s-$ or $R(9)-W_y-$;
s is zero, 1 or 2;

R(9) is H, methyl or ethyl;
w is oxygen or NR(10);
R(10) is H or methyl;
y is zero or 1; or
R(8) is $C_mF_{2m+1}$;
m is 1 to 3;
z is CO, $S(O)_s$ or $SO_2NR(13)$; or
R(6) is also hydrogen,
if one of the substituents R(1) to R(5) is R(8)—$C_nH_{2n}$—Z—;
wherein a methylene group in the —$C_nH_{2n}$— group is replaced by an oxygen or S atom or by an N atom;
n is zero to 7;
R(8) is hydrogen, $(C_3–C_6)$-alkenyl or $(C_5–C_8)$-cycloalkyl,
which is unsubstituted or substituted by 1 or 2 methyl groups or an OH group, and wherein a methylene group can be replaced by an oxygen or S atom or by an N atom; or
R(8) is pyridyl, quinolyl, isoquinolyl or phenyl,
unsubstituted or substituted by 1 to 3 substituents chosen from the group consisting of
F, Cl, Br, I, $CF_3$, $CH_3$—$S(O)_s$— or R(9)—$W_y$—;
s is zero, 1 or 2;
R(9) is H, methyl or ethyl;
W is oxygen or NR(10);
R(10) is H or methyl;
y is zero or 1; or
R(8) is $C_mF_{2m+1}$;
m is 1 to 3;
Z is O or NR(12);
R(7) is hydrogen, $(C_1–C_{10})$-alkyl, $(C_2–C_{10})$-alkenyl or R(8)—$C_nH_{2n}$—;
n is zero, 1, 2, 3 or 4;
R(8) is NR(14)R(15) or $CF_3$;
R(14) and R(15) are
hydrogen or methyl;
and pharmaceutically tolerated salts thereof.

Compounds of the formula I which are similarly especially preferred are those in which:
X is CR(6);
Y is NR(7);
A and B together are a bond or A and B are both hydrogen, if, at the same time, X is
CR(6) and Y is NR(7),
R(1) is —CO—N=C(NH$_2$)$_2$; the other respective substituents R(2) to R(5) are
hydrogen, F, Cl or Br,
or up to two of the other respective substituents R(2) to R(5) are
$(C_1–C_2)$-alkyloxy or $CF_3$;
or up to one of the other respective substituents R(2) to R(5) is
R(8)—$C_nH_{2n}$—Z—;
n is zero, 1 or 2,
wherein the alkylene chain —$C_nH_{2n}$— is straight-chain or branched;
R(8) is hydrogen, or
R(8) is pyridyl, quinolyl, isoquinolyl or phenyl,
unsubstituted or substituted by 1 to 3 substituents chosen from the group consisting of F, Cl, $CF_3$, $CH_3$—$S(O)_s$— or R (9)—$W_y$—;
s is zero or 2;
R(9) is H or methyl
W is oxygen,
y is zero or 1;
z is —CO—, —$CH_2$—, oxygen or —$S(O)_s$—;
s is zero or 2;
R(6) is defined as R(1) to R(5), but with the exception of hydrogen; or
R(6) is also hydrogen,
if one or two of the substituents R(1) to R(5) are $CF_3$; or
R(6) is also hydrogen,
if one of the substituents R(1) to R(5) is R(8)—$C_nH_{2n}$—Z—;
n is zero, 1 or 2;
R(8) is hydrogen, or
R(8) is pyridyl, quinolyl, isoquinolyl or phenyl,
unsubstituted or substituted by 1 to 3 substituents chosen from the group consisting of
F, Cl, Br, I, $CF_3$, $CH_3$—$S(IO)_s$— or R(9)—$W_y$—;
s is zero, 1 or 2;
R(9) is H or methyl;
W is oxygen;
y is zero or 1;
Z is CO, $S(O)_s$ or $SO_2NR(13)$; or
R(6) is also hydrogen,
if one of the substituents R(1) to R(5) is R(8)—$C_nH_{2n}$—Z—;
n is zero, 1 or 2;
R(8) is pyridyl, quinolyl, isoquinolyl or phenyl,
unsubstituted or substituted by 1 to 3 substituents chosen from the group consisting of
F, Cl, Br, I, $CF_3$, $CH_3$—S(O)S— or R(9)—$W_y$—;
s is zero, 1 or 2;
R(9) is H or methyl;
W is oxygen;
y is zero or 1;
Z is O or NR(12);
R(7) is hydrogen, $(C_1–C_6)$-alkyl, $(C_3–C_4)$-alkenyl or R(8)—$C_nH_{2n}$—;
n is zero, 1, 2, 3 or 4;
R(8) is NR(14)R(15) or $CF_3$;
R(14) and R(15) are hydrogen or methyl;
and pharmaceutically tolerated salts thereof.

Particularly preferred compounds are those chosen from the group consisting of:
3-chloro-1-methyl-2-indolylcarbonyl-guanidine hydrochloride,
3,5-dichloro-1-methyl-2-indolylcarbonyl-guanidine hydrochloride,
3-chloro-5-fluoro-1-methyl-2-indolylcarbonyl-guanidine hydrochloride,
4,6-dichloro-1,3-dimethyl-2-indolylcarbonyl-guanidine hydrochloride,
2-phenoxy-1-phenylindole-3-carboxylic acid guanidide methanesulfonic acid salt,
2-chloro-1-phenylindole-3-carboxylic acid guanidide methanesulfonic acid salt,
1-methylindoline-2-carboxylic acid guanidide hydrochloride,
5-fluoro-1-methylindoline-2-carboxylic acid guanidide hydrochloride.

The compounds I are substituted acylguanidines.

The most prominent representatives of the acylguanidines is the pyrazine derivative amiloride, which is used in therapy as a calcium-saving diuretic. Numerous other compounds of the amiloride type are described in the literature, such as, for example, dimethylamiloride or ethylisopropylamiloride.

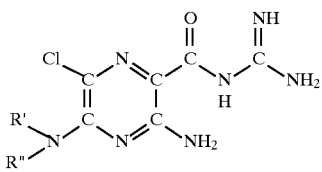

Amiloride: R', R"=H

Dimethylamiloride: R', R"=CH₃

Ethylisopropylamiloride: R'=C₂H₅, R"=CH(CH₃)₂

Studies which indicate antiarrhythmic properties of amiloride moreover have been disclosed (Circulation 79; 1257 to 1263 (1989)). However, wide use as an antiarrhythmic is impeded by the fact that this effect is only slight and occurs accompanied by an antihypertensive and saluretic action and these side effects are undesirable in the treatment of disturbances in cardiac rhythm.

Indications of antiarrhythmic properties of amiloride have also been obtained from experiments on isolated animal hearts (Eur. Heart J. 9 (supplement 1): 167 (1988) (book of abstracts)). Thus, for example, it has been found on rat hearts that it was possible to suppress an artificially induced ventricular fibrillation completely by amiloride. The above-mentioned amiloride derivative ethylisopropylamiloride was even more potent than amiloride in this model.

Benzoylguanidines having antiarrhythmic properties are described in European Offenlegungsschrift 416 499.

U.S. Pat. No. 3,780,027 also describes acylguanidines, which differ fundamentally from the compounds I according to the invention described here in that they are trisubstituted benzoylguanidines which are derived in their substitution pattern from commercially available diuretics, such as bumetanide and furosemide and have an amino group, which is important for the salidiuretic action sought, in position 2 or 3 relative to the carbonylguanidine group. A potent salidiuretic activity is correspondingly reported for these compounds.

It was therefore surprising that the compounds according to the invention have no undesirable and adverse salidiuretic properties but very good antiarrhythmic properties, such as occur, for example, with oxygen deficiency symptoms. As a result of their pharmacological properties, the compounds are outstandingly suitable as anti-arrhythmic medicaments having a cardioprotective component for prophylaxis of infarction and treatment of infarction and for treatment of angina pectoris, where they also preventively inhibit or greatly reduce the pathophysiological processes in the development of ischemically induced damage, in particular the initiation of ischemically induced cardiac arrhythmias. Because of their protective actions against pathological hypoxic and ischemic situations, the compounds of the formula I according to the invention, as a result of inhibition of the cellular Na+/H+ exchange mechanism, can be used as medicaments for the treatment of all acute or chronic damage caused by ischemia or diseases thereby induced primarily or secondarily. This applies to their use as medicaments for surgical interventions, for example organ transplants, where the compounds can be used both for protection of the organs in the donor before and during removal, for protection of organs removed, for example during treatment with or storage thereof in physiological bath fluids, and also during transfer to the recipient organism. The compounds are also valuable medicaments which have a protective action while angioplastic surgical interventions are carried out, for example on the heart and also on peripheral vessels. In accordance with their protective action against ischemically induced damage, the compounds are also suitable as medicaments for the treatment of ischemias of the nervous system, in particular the CNS, where they are suitable, for example, for the treatment of apoplexy or cerebral edema. The compounds of the formula I according to the invention moreover are also suitable for treatments of forms of shock, such as, for example, allergic, cardiogenic, hypovolemic and bacterial shock.

The compounds of the formula I according to the invention furthermore are distinguished by a potent inhibiting action on the proliferations of cells, for example fibroblast cell proliferation and proliferation of smooth vascular muscle cells. The compounds of the formula I are therefore possible valuable therapeutics for diseases in which cell proliferation is a primary or secondary cause, and they can therefore be used as antiatherosclerotics and as agents against delayed diabetic complications, cancer diseases, fibrotic diseases, such as pulmonary fibrosis, hepatic fibrosis or renal fibrosis, and organ hypertrophies and hyperplasias, in particular prostate hyperplasia or prostate hypertrophy.

The compounds according to the invention are effective inhibitors of the cellular sodium/proton antiport (Na+/H+ exchanger), which, in numerous diseases (essential hypertension, atherosclerosis, diabetes and the like) is also increased in those cells which are readily accessible for measurements, such as, for example, in erythrocytes, platelets or leukocytes. The compounds according to the invention are therefore suitable as outstanding and simple scientific tools, for example in their use as diagnostics for determination and differentiation of certain forms of hypertension, but also of atherosclerosis, diabetes, proliferative diseases and the like. The compounds of the formula I furthermore are suitable for preventive therapy for prevention of the origin of high blood pressure, for example essential hypertension.

The invention furthermore relates to a process for the preparation of the compounds I, which comprises reacting compounds of the formula II

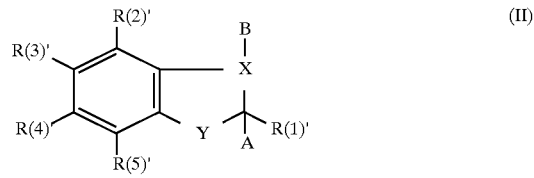

in which one of the substituents R(1)' to R(5)' is a —CO—L group and L is a leaving group which can easily be replaced nucleophilically, and the other respective substituents R(1)' to R(5)' have the meaning given, with guanidine to form the acylguanidine group shown in formula I,
—CO—N═C(NH₂)₂ and, if appropriate, converting the product into the pharmacologically tolerated salt.

The activated acid derivatives of the formula II in which L is an alkoxy, preferably a methoxy group, a phenoxy group, a phenylthio, methylthio or 2-pyridylthio group or a nitrogen-containing heterocyclic ring, preferably 1-imidazolyl, are advantageously obtained in a manner known per se from the carboxylic acid chlorides on which they are based (formula II, L=Cl), which in turn can be prepared, again in a manner known per se, from the carboxylic acids on which they are based (formula II, L=OH), for example with thionyl chloride.

In addition to the carboxylic acid chlorides of the formula II (L=Cl), other activated acid derivatives of the formula II can also be prepared directly in a manner known per se from the heterocyclic carboxylic acid derivatives on which they are based (formula II, L=OH), such as, for example, the methyl esters of the formula II, where L=OCH$_3$, by treatment with gaseous HCl in methanol, the imidazolides of the formula II by treatment with carbonyldiimidazole (L=1-imidazolyl, Staab, Angew. Chem. Int. Ed. Engl. 1, 351 to 367 (1962)), the mixed anhydrides II with Cl-COOC$_2$H$_5$ or tosyl chloride in the presence of triethylamine in an inert solvent, and also the activations of carboxylic acids with dicyclohexylcarbodiimide (DCC). A number of suitable methods for the preparation of activated carboxylic acid derivatives of the formula II are mentioned with reference to source literature in J. March, Advanced Organic Chemistry, Third Edition (John Wiley & Sons, 1985), page 350.

The reaction of an activated carboxylic acid derivative of the formula I with guanidine is carried out in a manner known per se in a protic or aprotic polar but inert organic solvent. Methanol or tetrahydrofuran between 20° C. and the boiling point have proved suitable as solvents for the reaction of the carboxylic acid methyl esters (II, L=OMe) with guanidine. Most of the reactions of compounds II with guanidine have advantageously been carried out in aprotic inert solvents, such as tetrahydrofuran, dimethoxyethane or dioxane. However, water can also be used as the solvent for the reaction of II and guanidine.

If L is Cl, the reaction is advantageously carried out with the addition of an acid-trapping agent, for example in the form of excess guanidine to bond the hydrogen halide acid.

Some of the heterocyclic carboxylic acid derivatives on which the compounds are based are known and are described in the literature. The heterocyclic carboxylic acids II (L=OH) which are not known can be prepared by methods known from the literature.

Thus, for example, the 2-benzimidazolecarboxylic acids [formula II with R(1)=—COOH, X=N and Y=—NR(7)], which lead to preferred compounds according to the invention, are obtained in a manner known per se by oxidation of the corresponding 2-hydroxymethylbenzimidazoles with potassium permanganate by a method analogous to that of Bistrzycki and Przeworski (Ber. 45, 3483 [1912]).

The indole-2-carboxylic acids which lead to preferred carbonylguanidines of the formula I are obtained, for example, from the 2-nitrotoluenes by the method of J. R. Johnson et al. J. Am. Chem. Soc. 67, 423 (1945) [see also Noland and Baude, Org. Synth. Coll. Vol. 5, 567 (1973)], and by the Fischer indole synthesis from pyruvic acid and phenylhydrazone. Another preparation method for indole-2-carboxylic acids is the bromoform or iodoform reaction of 2-acetylindoles, which can be carried out by the method of Rajur et al., Synth. Commun. 22, 421–428 (1992). A preparation method from 2-ketoanilines is described by Jones et al. (J. Org. Chem 37, 3622 [1972]).

Starting materials for the preparation of specifically substituted indole-2-carboxylic acids can also be indole-2-carboxylic acids themselves, onto which substitution reactions are easily carried out in a manner known from the literature. Numerous electrophilic substitution reactions in the 3-position and also in the remaining positions can be carried out particularly selectively in this case. Thus, for example, halogenations proceed smoothly with a Hal$^+$ transfer agent and with a complete conversion. Alkylation and arylation reactions likewise can be carried out very easily on the nitrogen atom in the 1-position.

The indoline-2-carboxylic acids and esters thereof can be obtained generally in a manner known from the literature from the indole-2-carboxylic acids or esters thereof on which they are based by reduction or hydrogenation. Treatment with metallic magnesium in methanol analogously to the working procedure of Kwon Youn, Gyu Hwan Yon, Chwang Siek Pak; Tetrahedron Letters 27 (1986) 2409–2410 has proved to be particularly suitable.

Benzoylguanidines I are in general weak bases and can bond acid to form salts. Possible acid addition salts are salts of all the pharmacologically tolerated acids, for example halides, in particular hydrochlorides, lactates, sulfates, citrates, tartrates, acetates, phosphates, sulfonic acid salts, such as methylsulfonates, p-toluene-sulfonates and the like.

Medicaments which comprise a compound I can be administered here orally, parenterally, intravenously or rectally or by inhalation, the preferred administration depending on the particular clinical picture of the disease. The compounds I can be used here by themselves or together with galenical auxiliaries, and in particular both in veterinary and in human medicine.

The expert is familiar with the auxiliaries which are suitable for the desired medicament formulation on the basis of his expert knowledge. In addition to solvents, gel-forming agents, suppository bases, tablet auxiliaries and other active compound carriers, for example, antioxidants, dispersing agents, emulsifiers, defoamers, flavor correctants, preservatives, solubilizing agents or dyestuffs can be used.

For an oral use form, the active compounds are mixed with the additives suitable for this form, such as carrier substances, stabilizers or inert diluents, and are brought by the customary methods into the suitable dosage forms, such as tablets, coated tablets, push-fit capsules or aqueous, alcoholic or oily solutions. Inert carriers which can be used are, for example, gum arabic, magnesia, magnesium carbonate, potassium phosphate, lactose, glucose or starch, in particular maize starch. The mixture can be formulated either as dry or as moist granules. Possible oily carrier substances or possible solvents are, for example, vegetable or animal oils, such as sunflower oil or cod liver oil.

For subcutaneous or intravenous administration, if desired, the active compounds are dissolved, suspended or emulsified with the substances customary for this purpose, such as solubilizing agents, emulsifiers or other auxiliaries. Possible solvents are, for example: water, physiological saline solution or alcohols, for example ethanol, propanol or glycerol, and in addition also sugar solutions, such as glucose solutions or mannitol solutions, or also a mixture of the various solvents mentioned.

Suitable pharmaceutical formulations for administration in the form of aerosols or sprays are, for example, solutions, suspensions or emulsions of the active compound of the formula I in a pharmaceutically acceptable solvent, such as, in particular ethanol or water, or a mixture of such solvents. If required, the formulation can also additionally comprise other pharmaceutical auxiliaries, such as surfactants, emulsifiers and stabilizers, and a propellant gas. Such a formulation usually comprises the active compound in a concentration of about 0.1 to 10, in particular about 0.3 to 3% by weight.

The dosage of the active compound of the formula I to be administered and the frequency of administration depend on the action potency and duration of action of the compounds used; and furthermore also on the nature and severity of the disease to be treated and on the sex, age, weight and individual response of the mammal to be treated.

On average, the daily dose of a compound of the formula I for a patient weighing about 75 kg is at least 0.001 mg, preferably 0.01 mg to not more than 10 mg, preferably not more than 1 mg. For acute outbreaks of the disease, for example immediately after suffering cardiac infarction, even higher and above all more frequent dosages may also be necessary, for example up to 4 individual doses per day. Up to 100 mg per day may be necessary, especially with i.v. use, for example on an infarction patient in intensive care.

EXAMPLES

General instructions I for preparation of heterocyclic acylguanidines (I) from heterocyclic carboxylic acids (II, L=OH)

0.01M of the carboxylic acid derivative of the formula II (L=OH) is dissolved or suspended in 60 ml of anhydrous tetrahydrofuran (THF), and 1.78 g (0.011M) of carbonyldiimidazole are then added. After the mixture has been stirred at room temperature for 2 hours, 2.95 g (0.05M) of guanidine are introduced into the reaction solution. After the mixture has been stirred overnight, the THF is distilled off under reduced pressure (rotary evaporator), water is added, the pH is brought to 6–7 with 2N HCl and the corresponding acylguanidine (formula I) is filtered off.

The heterocyclic acylguanidines thus obtained can be converted into the corresponding salts by treatment with aqueous or methanolic hydrochloric acid or other pharmacologically tolerated salts.

General instructions II for preparation of heterocyclic acylguanidines (I) from the corresponding carboxylic acid esters (formula II, L=alkoxy or phenoxy)

1 equivalent of a corresponding carboxylic acid ester of the formula II and 5.0 equivalents of guanidine are dissolved in isopropanol or suspended in THF and the solution or suspension is boiled under a reflux condenser until the reaction is complete (monitoring by thin layer chromatography; reaction time about 2–8 hours). The solvent is distilled off under reduced pressure (rotary evaporator), the residue is taken up in ethyl acetate and the mixture is washed 3 times with saturated sodium bicarbonate solution.

Drying of the organic phase over sodium sulfate, removal of the solvent by distillation under reduced pressure and chromatography of the residue over silica gel using a suitable mobile phase.

Conversion of the corresponding heterocyclic acylguanidine of the formula I obtained into the corresponding hydrochloride is carried out analogously to instructions I.

The following compounds according to the invention were prepared in accordance with the general instructions I and II:

Example 1

2-Benzofurylcarbonyl-guanidine hydrochloride,
Melting point 279°–283° C.

Example 2

6-Chloro-2-benzofurylcarbonyl-guanidine hydrochloride,
Melting point 272°–274° C.

Example 3

7-Methoxy-2-benzofurylcarbonyl-guanidine hydrochloride,
Melting point 266° C.

Example 4

7-Bromo-4-hydroxy-3-benzofurylcarbonyl-guanidine hydrochloride,
Melting point 239° C.

Example 5

7-Hydroxy-2-benzofurylcarbonyl-guanidine hydrochloride,
Melting point 243°–244° C.

Example 6

5-Dimethylaminomethyl-2-benzofurylcarbonyl-guanidine dihydrochloride,
Melting point >250° C.

Example 7

5,6-Dichloro-2-benzofurylcarbonyl-guanidine hydrochloride,
Melting point >250° C.

Example 8

7-Amino-2-benzothiazolylcarbonyl-guanidine dihydrochloride,
Melting point >250° C.

Example 9

2-Amino-6-benzothiazolylcarbonyl-guanidine dihydrochloride,
Melting point >250° C.

Example 10

6-Chloro-3-methoxybenzo[b]thien-2-ylcarbonyl-guanidine hydrochloride,
Melting point 202° C.

Example 11

Benzotriazol-5-ylcarbonyl-guanidine hydrochloride,
Melting point 270° C.

Example 12

2-Benzothiazolylcarbonyl-guanidine hydrochloride,
Melting point 273°–275° C.

Example 13

Benzo[b]thien-2-ylcarbonyl-guanidine hydrochloride,
Melting point 296°–298° C.

Example 14

2-Chloro-5-methylbenzo[b]thien-2-ylcarbonyl-guanidine hydrochloride,
Melting point 221°–222° C.

Example 15

5-Nitrobenzo[b]thien-2-ylcarbonyl-guanidine hydrochloride,
Melting point 285° C.

Example 16

5-Aminobenzo[b]thien-2-ylcarbonyl-guanidine hydrochloride,
Melting point 250° C. (decomposition).

Example 17

1H-Benzimidazol-5-yl-carbonyl-guanidine hydrochloride,
Melting point 265° C.

Example 18

1-(2-Chlorobenzyl)-1H-benzimidazol-5-yl-carbonyl-guanidine hydrochloride,
Melting point 265° C.

Example 19

1-(1-Hexyl)-1H-benzimidazol-5-yl-carbonyl-guanidine hydrochloride,
Melting point 232°–234° C.

Example 20

1-(2-Chlorobenzyl)-2-hydroxy-1H-benzimidazol-5-yl-carbonyl-guanidine hydrochloride,
Melting point 283° C.

Example 21

2-Methylthio-1H-benzimidazol-5-yl-carbonyl-guanidine hydrochloride,
Melting point 211° C.

Example 22

1-(2-Chlorobenzyl)-2-methylthio-1H-benzimidazol-5-yl-carbonyl-guanidine hydrochloride,
Melting point 220° C.

Example 23

1-(1-Hexyl)-2-hydroxy-1H-benzimidazol-5-yl-carbonyl-guanidine hydrochloride,
Melting point 227°–229° C.

Example 24

6-[N-Methyl-N-(2-phenylethyl)sulfamoyl]-1H-benzimidazol-4-yl-carbonyl-guanidine hydrochloride,
Melting point 205° C.

Example 25

1-Methyl-2-methylthio-1H-benzimidazol-6-yl-carbonyl-guanidine hydrochloride,
Melting point 246° C.

Example 26

6-Sulfamoyl-1H-benzimidazol-4-yl-carbonyl-guanidine hydrochloride,
Melting point 223° C.

Example 27

2-(2-Phenylethyl)-6-N-pyrrolidinosulfonyl-1H-benzimidazol-4-yl-carbonyl-guanidine hydrochloride,
Melting point 192° C. (decomposition).

Example 28

6-Chloro-2-(2-phenylethyl)-1H-benzimidazol-4-yl-carbonyl-guanidine hydrochloride,
Melting point 262°–264° C.

Example 29

6-N-Pyrrolidinosulfonyl-1H-benzimidazol-4-yl-carbonyl-guanidine hydrochloride,
Melting point 200°–202° C. (decomposition).

Example 30

6-Methylsulfonyl-2-(2-phenylethyl)-1H-benzimidazol-4-yl-carbonyl-guanidine hydrochloride,
Melting point 215° C.

Example 31

6-[N-Methyl-N-(2-phenylethyl)sulfamoyl]-2-(2-phenylethyl)-1H-benzimidazol-4-yl-carbonyl-guanidine hydrochloride,
Melting point 130° C.

Example 32

2-Benzylthio-6-methylsulfonyl-1H-benzimidazol-4-yl-carbonyl-guanidine hydrochloride,
Melting point 215° C.

Example 33

5-Chloro-1-methyl-1H-benzimidazol-2-yl-carbonyl-guanidine hydrochloride,
Melting point 228° C.

Example 34

5,6-Dichloro-1-methyl-1H-benzimidazol-2-yl-carbonyl-guanidine hydrochloride,
Melting point 274° C. (decomposition)

Example 35

3-Indolylcarbonyl-guanidine hydrochloride,
Melting point 270° C. (decomposition)

Example 36

5-Indolylcarbonyl-guanidine hydrochloride,
Melting point 258° C. (decomposition)

Example 37

1-Benzyl-3-indolylcarbonyl-guanidine hydrochloride,
Melting point 256° C. (decomposition)

Example 38

4-Indolylcarbonyl-guanidine hydrochloride,
Melting point 270° C. (decomposition)

Example 39

1-Methyl-3-indolylcarbonyl-guanidine hydrochloride,
Melting point 250° C. (decomposition)

Example 40

1-(2-N,N-Dimethylaminoethyl)-3-indolylcarbonyl-guanidine dihydrochloride,
Melting point 250° C. (decomposition)

Example 41

1-Methyl-2-indolylcarbonyl-guanidine hydrochloride,
Melting point 280° C.

Example 42

2-Indolylcarbonyl-guanidine hydrochloride,
Melting point 310°–312° C.

Example 43

5-Chloro-2-indolylcarbonyl-guanidine hydrochloride,
Melting point 317°–320° C.

Example 44

5-Methoxy-2-indolylcarbonyl-guanidine hydrochloride,
Melting point 292° C.

Example 45

5-Chloro-1-methyl-2-indolylcarbonyl-guanidine hydrochloride,
Melting point 269° C.

Example 46

1-(3,4-Dichlorobenzyl)-2-indolylcarbonyl-guanidine hydrochloride,
Melting point 195° C.

Example 47

1-(2-N,N-Dimethylaminoethyl)-2-indolylcarbonyl-guanidine dihydrochloride,
Melting point 255° C. (decomposition)

Example 48

1-Benzyl-2-indolylcarbonyl-guanidine hydrochloride,
Melting point 229° C.

Example 49

1-Ethyl-2-indolylcarbonyl-guanidine hydrochloride,
Melting point 200°–201° C.

Example 50

1-Benzyl-5-chloro-2-indolylcarbonyl-guanidine hydrochloride,
Melting point 198° C.

Example 51

5-Chloro-1-(2-N,N-dimethylaminoethyl)-2-indolylcarbonyl-guanidine dihydrochloride,
Melting point 255° C. (decomposition)

Example 52

5-Chloro-1-ethyl-2-indolylcarbonyl-guanidine hydrochloride,
Melting point 255° C.

Example 53

5-Chloro-1-propyl-2-indolylcarbonyl-guanidine hydrochloride,
Melting point 255° C.

Example 54

5-Chloro-1-butyl-2-indolylcarbonyl-guanidine hydrochloride,
Melting point 222° C.

Example 55

5-Hydroxy-1-methyl-2-indolylcarbonyl-guanidine hydrochloride,
Melting point 288° C.

Example 56

3,5-Dichloro-1-(2-N,N-dimethylaminoethyl)-2-indolylcarbonyl-guanidine dihydrochloride,
Melting point 246° C.

Example 57

5-Methoxy-1-methyl-2-indolylcarbonyl-guanidine hydrochloride,
Melting point 227° C.

Example 58

3-Chloro-1-methyl-2-indolylcarbonyl-guanidine hydrochloride,
Melting point 216° C.

Example 59

3-Chloro-2-indolylcarbonyl-guanidine hydrochloride,
Melting point 222° C.

Example 60

3,5-Dichloro-1-(4-picolyl)-2-indolylcarbonyl-guanidine hydrochloride,
Melting point 220° C.

Example 61

5-Chloro-1-(4-picolyl)-2-indolylcarbonyl-guanidine hydrochloride,
Melting point 287° C.

Example 62

5-Chloro-1,3-dimethyl-2-indolylcarbonyl-guanidine hydrochloride,
Melting point 258° C.

Example 63

5,7-Dichloro-1,3-dimethyl-2-indolylcarbonyl-guanidine hydrochloride,
Melting point 307° C.

Example 64

4,6-Dichloro-1,3-dimethyl-2-indolylcarbonyl-guanidine hydrochloride,
Melting point 296° C.

Example 65

5-Chloro-1-methyl-3-phenyl-2-indolylcarbonyl-guanidine hydrochloride,
Melting point 288° C.

Example 66

3-Bromo-1-methyl-2-indolylcarbonyl-guanidine hydrochloride,
Melting point 208°–210° C.

Example 67

5-Fluoro-1-methyl-2-indolylcarbonyl-guanidine hydrochloride,
Melting point 278° C.

Example 68

3,5-Dichloro-2-indolylcarbonyl-guanidine hydrochloride,
Melting point 208°–210° C.

Example 69

3,5-Dichloro-1-methyl-2-indolylcarbonyl-guanidine hydrochloride,
Melting point 208°–210° C.

Example 70

4,5,6-Trichloro-1,3-dimethyl-2-indolylcarbonyl-guanidine hydrochloride,
Melting point 307° C.

Example 71

2-(4-Methoxyphenyl)-benzimidazole-5-carboxylic acid guanidide methanesulfonic acid salt;
Melting point 270° C.

Example 72

2-(4-Trifluoromethylphenyl)-benzimidazole-5-carboxylic acid guanidide methanesulfonic acid salt;
Melting point 275° C.

Example 73

2-Phenylbenzimidazole-4-carboxylic acid guanidide
Melting point 264° C.

Example 74

2-(4-Fluorophenyl)-1-methylbenzimidazole-5-carboxylic acid guanidide methanesulfonic acid salt;
Melting point 252° C.

Example 75

2-(4-Methylphenyl)-benzimidazole-5-carboxylic acid guanidide methanesulfonic acid salt;
Melting point 285° C.

Example 76

2-(4-Hydroxyphenyl)-benzimidazole-4-carboxylic acid guanidide methanesulfonic acid salt;
Melting point 281° C.

Example 77

2-[4-(4-Chlorophenoxy)phenyl]-benzimidazole-5-carboxylic acid guanidide methanesulfonic acid salt;
Melting point 239° C.

Example 78

2-Benzylbenzimidazole-5-carboxylic acid guanidide methanesulfonic acid salt;
Melting point 210° C.

Example 79

2-Undecylbenzimidazole-5-carboxylic acid guanidide methanesulfonic acid salt;
Melting point 252° C.

Example 80

2-Methylbenzimidazole-5-carboxylic acid guanidide methanesulfonic acid salt;
Melting point 279° C.

Example 81

1-Methyl-2-phenylbenzimidazole-5-carboxylic acid guanidide methanesulfonic acid salt;
Decomposition point: 230° C.

Example 82

1-Methyl-2-(2-thienyl)benzimidazole-5-carboxylic acid guanidide methanesulfonic acid salt;
Melting point 211° C.

Example 83

2-Chloro-1-phenylindole-3-carboxylic acid guanidide methanesulfonic acid salt;
Melting point 203°–205° C.

Example 84

2-Phenoxy-1-phenylindole-3-carboxylic acid guanidide methanesulfonic acid salt;
Melting point 202°–204° C.

Example 85

5-Chloro-1-ethylbenzimidazole-2-carboxylicacidguanidide hydrochloride;
Melting point: 244° C.

Example 86

3-Chloro-5-fluoro-1-methylindolyl-2-carboxylic acid guanidide hydrochloride;
Melting point: 234° C.

Example 87

5-Methoxy-1-phenylindolyl-2-carboxylic acid guanidide hydrochloride;
Melting point 266° C.

Example 88

3-Isopropyl-5-methoxyindolyl-2-carboxylic acid guanidide hydrochloride;
Melting point: 210° C.

Example 89

5-Chloro-3-phenylthio-2-indolylcarboxylic acid guanidide hydrochloride;
Melting point: 252° C.

Example 90

3,5-Dimethoxy-1-methyl-2-indolylcarboxylic acid guanidide methanesulfonic acid salt;
Melting point: 212° C.

Example 91

3-Isopropoxy-5-methoxy-1-methyl-2-indolylcarboxylic acid guanidide methanesulfonic acid salt;
Melting point 248° C.

Example 92

5-Chloro-3-phenylsulfonyl-2-indolylcarboxylic acid guanidide methanesulfonic acid salt;

Melting point 240° C.

Example 93

5-Chloro-1-phenyl-2-indolylcarboxylic acid guanidide methanesulfonic acid salt;

Decomposition point: 305° C.

Example 94

5-Chloro-3-isopropyl-2-indolylcarboxylic acid guanidide methanesulfonic acid salt;

Decomposition point: 258°–259° C.

Example 95

5-Chloro-3-methoxy-1-methyl-2-indolylcarboxylic acid guanidide methanesulfonic acid salt;

Decomposition point: 234° C.

Example 96

5-Chloro-3-isopropyl-1-methyl-2-indolylcarboxylic acid guanidide methanesulfonic acid salt;

Decomposition point: 164°–166° C.

Example 97

5-Trifluoromethyl-3-methyl-2-indolylcarboxylic acid guanidide hydrochloride;

Decomposition point: 232°–236° C.

Example 98

5-Trifluoromethyl-1,3-dimethyl-2-indolylcarboxylic acid guanidide hydrochloride;

Decomposition point: 219°–223° C.

Example 99

5-Benzoyl-1,3-dimethyl-2-indolylcarboxylic acid guanidide hydrochloride;

Melting point 270°–273° C.

Example 100

5-Cyclohexyl-1,3-dimethyl-2-indolylcarboxylic acid guanidide hydrochloride;

Melting point 191°–194° C.

Example 101

1,3,5-Trimethyl-2-indolylcarboxylic acid guanidide hydrochloride;

Melting point 210°–212° C.

Example 102

1,3,4,6-Tetramethyl-2-indolylcarboxylic acid guanidide hydrochloride;

Decomposition point: 164°–171° C.

Example 103

5-Methylsulfonyl-2-indolylcarboxylic acid guanidide hydrochloride;

Melting point 298°–305° C.

Example 104

1-Methylindoline-2-carboxylic acid guanidide hydrochloride:

a) Indoline-2-carboxylic acid was reacted with 2equivalents of $K_2CO_3$ and methyl iodide in dimethylformamide to give methyl N-methyl-indoline-2-carboxylate.

Colorless oil; MS (ES): 192 (M+1)

The ester from a) was heated under reflux with 5equivalents of guanidine in tetrahydrofuran. The solvent was stripped off in vacuo, the residue was taken up in water and the mixture was extracted three times with ethyl acetate. The combined organic phases were dried over $MgSO_4$ and the resulting guanidide was isolated as the hydrochloride by addition of methanolic HCR.

Solid, melting point 162°–170° C.

Example 105

1-Methyl-(S)-indoline-2-carboxylic acid guanidide hydrochloride

Was prepared in an analogous manner from (S)-indoline-2-carboxylic acid.

Solid, melting point 162° C.

Example 106

5-Fluoro-1-methylindoline-2-carboxylic acid guanidide hydrochloride a) Methyl 5-fluoro-indole-2-carboxylate was reacted with magnesium in methanol in accordance with instructions known from the literature [In Kwon Youn, Gyu Hwan Yon, Chwang Siek Pak; Tetrahedron Letters 27 (1986) 2409–2410] to give methyl 5-fluoro-indoline-2-carboxylate.

Colorless oil; MS (ES): 196 (M+1)

b) The indoline-2-carboxylic acid ester from reaction a) was N-methylated with $K_2CO_3$ and methyl iodide in dimethylformamide. After standard working up, methyl N-methyl-5-fluoro-indoline-2-carboxylate was isolated.

Colorless oil; MS (ES): 210 (M+1)

c) The product from reaction b) was heated under reflux with 5 equivalents of guanidine in THF. The solvent was stripped off in vacuo, the residue was taken up in water and the mixture was extracted three times with ethyl acetate. The combined organic phases were dried over $MgSO_4$ and the resulting guanidide was isolated as the hydrochloride by addition of methanolic HCl.

Reddish solid, melting point 135°–150° C.

Example 107

5-Methoxy-1-methylindoline-2-carboxylic acid guanidide hydrochloride was prepared in an analogous manner.

Reddish solid, melting point 169°–174° C.

This transformation of indole-2-carboxylic acid derivatives into the corresponding indoline derivatives in Examples 104 to 107 can also be applied to all the other indole-carboxylic acids.

Example 108

1-Methylindole-2-carboxylic acid guanidide is obtained by treatment of a suspension of 1.5 g of 1-methylindole-2-carboxylic acid guanidide hydrochloride in 30 ml of water with aqueous sodium bicarbonate solution.

Colorless crystals, melting point 95°–100° C.

PREPARATION METHODS FOR PRECURSORS

A. 3-Iodoindole-2-carboxylic acid derivatives are obtained, for example, by dropwise addition of a solution of 0.02 mol of iodine monochloride in glacial acetic acid to a solution or suspension of 0.02 mol of indole-2-carboxylic acid ester at room temperature and subsequent stirring at 40° C. for 30 minutes. After the solvent has been distilled off, the residue is taken up in water and the crystalline solid is filtered off.

Ethyl 5-chloro-3-iodoindole-2-carboxylate: colorless crystals, melting point 190°–194° C.

Ethyl 3-iodoindole-2-carboxylate: colorless crystals, melting point 127°–131° C.

5-Benzyloxy-3-iodoindole-2-carboxylate: colorless crystals, melting point 122°–1240C.

5-Fluoro-3-iodoindole-2-carboxylate: colorless crystals, melting point 154°–158° C.

B. 3-Bromoindole-2-carboxylic acid derivatives are obtained, for example, by dropwise addition of a solution of 0.05 mol of bromine in glacial acetic acid to a solution or suspension of 0.05 mol of indole-2-carboxylic acid ester at room temperature and subsequent stirring at 40° C. for a further 15 minutes. After the solvent has been distilled off, the residue is taken up in water, the crystalline solid is filtered off and the 3-bromoindole-2-carboxylic acid ester is purified by recrystallization.

Example B1

Ethyl 3-bromoindole-2-carboxylate: colorless crystals, melting point 143°–144° C.

Example B2

Ethyl 3-bromo-5-chloroindole-2-carboxylate: colorless crystals, melting point 184°–186° C.

C. 3-Chloroindole-2-carboxylic acid derivatives are obtained, for example, by dropwise addition of a solution of 0.05 mol of N-chlorosuccinimide in glacial acetic acid to a solution or suspension of 0.05 mol of indole-2-carboxylic acid ester at room temperature, subsequent stirring at 40° C. for a further 15 minutes and subsequent after-stirring at room temperature. After the solvent has been distilled off, the residue is taken up in water and the pH is brought to 8 with saturated aqueous sodium bicarbonate solution. The crystalline solid is filtered off and the 3-chloroindole-2-carboxylic acid ester is purified by recrystallization.

Example C1)

Ethyl 3,5-dichloroindole-2-carboxylate; colorless crystals, melting point 163°–165° C.

Example C2)

Ethyl 3-chloro-5-fluoroindole-2-carboxylate; colorless crystals, melting point 138°–141° C.

Example C3)

Ethyl 3-bromo-5-chloroindole-2-carboxylate, crystalline solid, melting point 178°–182° C.

D. 1-Alkylations of 2-indolecarbonyl derivatives are carried out, for example, by a procedure in which a mixture of 0.05 mol of the particular indole-2-carboxylic acid ester, 0.06 mol of alkylating agent and 0.015 mol of finely powdered, anhydrous potassium carbonate in 10 to 50 ml of acetone is boiled under a reflux condenser for about 5–8 hours and the progress of the reaction is monitored by thin layer chromatography. The solvent is then distilled off, water is added to the residue and the mixture is extracted with ethyl acetate.

Example D1)

Ethyl 3-iodo-1-methylindole-2-carboxylate:
Alkylating agent: methyl iodide;
Properties: pale yellow oil.

Example D2)

Ethyl 5-chloro-3-iodo-1-methylindole-2-carboxylate:
Alkylating agent: methyl iodide;
Properties: colorless crystalline substance, melting point 88°–93° C.

Example D3)

Ethyl 3-iodo-1-(2-dimethylaminoethyl)indole-2-carboxylate:
Alkylating agent: 2-dimethylaminoethyl chloride hydrochloride;
Properties: pale yellow oil.

Example D4)

Ethyl 3-iodo-1-(3,4-dichlorobenzyl)indole-2-carboxylate:
Alkylating agent: 3,4-dichlorobenzyl chloride;
Properties: pale yellow oil.

Example D5)

Ethyl 5-chloro-1-ethyl-3-iodoindole-2-carboxylate:
Alkylating agent: ethyl bromide
Properties: colorless, crystalline solid, melting point 56°–59° C.

Example D6)

Ethyl 5-chloro-3-iodo-1-propylindole-2-carboxylate:
Alkylating agent: propyl iodide
Properties: colorless, crystalline solid, melting point 77°–84° C.

Example D7)

Ethyl 1-butyl-5-chloro-3-iodoindole-2-carboxylate:
Alkylating agent: butyl iodide
Properties: pale yellow oil.

Example D8)

Ethyl 5-chloro-3-iodo-1-isopropylindole-2-carboxylate:
Alkylating agent: isopropyl iodide
Properties: colorless, crystalline solid, melting point 162°–166° C.

Example D9)

Ethyl 5-benzyloxy-3-iodo-1-methylindole-2-carboxylate:
Alkylating agent: methyl iodide
Properties: colorless, crystalline solid, inexact melting point 90°–105° C.

Example D10)

Ethyl 5-fluoro-3-iodo-1-methylindole-2-carboxylate:
Alkylating agent: methyl iodide
Properties: colorless, crystalline solid, inexact melting point 76°–79° C.

Example D11)

Ethyl 3,5-dichloro-1-methylindole-2-carboxylate:
Alkylating agent: methyl iodide
Properties: colorless, crystalline solid, inexact melting point 54°–56° C.

Example D12)

Ethyl 3,5-dichloro-1-(2-dimethylaminoethyl)indole-2-carboxylate:

Alkylating agent: 2-dimethylaminoethyl chloride hydrochloride

Properties: oil.

Example D13)

Ethyl 3,5-dichloro-1-(4-picolyl)indole-2-carboxylate:
Alkylating agent: 4-picolyl chloride hydrochloride
Properties: melting point 100°–103° C.

Example D14)

Ethyl 5-chloro-3-iodo-1-(4-picolyl)indole-2-carboxylate:
Alkylating agent: 4-picolyl chloride hydrochloride
Properties: melting point 127°–129° C.

Example D15)

2-Acetyl-5-chloro-1,3-dimethylindole
Alkylating agent: methyl iodide
Properties: melting point 88° C.

Example D16)

2-Acetyl-5-chloro-1-methyl-3-phenylindole
Alkylating agent: methyl iodide
Properties: melting point 89°–91° C.

Example D17)

2-Acetyl-5,7-dichloro-1,3-dimethylindole
Alkylating agent: methyl iodide
Properties: melting point 105°–108° C.

Example D18)

2-Acetyl-4,6-dichloro-1,3-dimethylindole
Alkylating agent: methyl iodide
Properties: melting point 115°–118° C.

Example D19)

2-Acetyl-4,5,6-trichloro-1,3-dimethylindole
Alkylating agent: methyl iodide
Properties: melting point 129° C.

Example D20)

Ethyl 5-fluoro-3-chloro-1-methylindole-2-carboxylate:
Alkylating agent: methyl iodide
Properties: colorless, crystalline solid, inexact melting point 65°–69° C.

Example D21)

Methyl 5-chloro-3-phenylsulfonyl-1-methylindole-2-carboxylate by methylation of 5-chloro-3-phenylsulfonylindole-2-carboxylic acid
Alkylating agent: methyl iodide
Properties: colorless, crystalline solid, melting point 192°–196° C.

Example D22)

Ethyl 3-bromo-5-chloro-1-methylindole-2-carboxylate by the alkylating agent: methyl iodide
Properties: colorless, crystalline solid, melting point 60°–63° C.

Example D23)

2-Acetyl-5-isopropyl-1,3-dimethylindole
Alkylating agent: methyl iodide
Properties: colorless, crystalline solid, melting point 74°–77° C.

Example D23a)

2-Acetyl-5-benzoyl-1,3-dimethylindole
Alkylating agent: methyl iodide
Properties: colorless, crystalline solid, melting point 113° C.

Example D24)

2-Acetyl-5-benzoyl-1,3,5-trimethylindole
Alkylating agent: methyl iodide
Properties: colorless, crystalline solid, melting point 175° C.

E. Preparation of 1-alkylcarboxylic acid derivatives by dehalogenating hydrogenation were preferably carried out with 3-iodo or 3-bromoindole- 2-carboxylic acid derivatives:

0.005 mol of the 3-halogenoindole-2-carboxylic acid ester are hydrogenated in methanol with 300 mg of palladium-on-charcoal (10%), while shaking at room temperature, until the theoretical uptake of hydrogen is reached, the solvent is distilled off and water is added to the residue.

Example E1)

Ethyl 5-chloro-1-methylindole-2-carboxylate
Properties: colorless, crystalline substance, melting point 68°–72° C.

Example E2)

Ethyl 1-(2-dimethylaminoethyl)indole-2-carboxylate
Properties: pale yellow oil.

Example E3)

Ethyl 1-(3,4-dichlorobenzyl)indole-2-carboxylate
Properties: colorless, crystalline solid; melting point 88°–92° C.

Example E4)

Ethyl 5-chloro-1-ethylindole-2-carboxylate
Properties: colorless, crystalline substance, melting point 53°–56° C.

Example E5)

Ethyl 1-isopropyl-5-chloroindole-2-carboxylate
Properties: colorless, crystalline substance, melting point 151°–155° C.

Example E6)

Ethyl 5-chloro-1-propylindole-2-carboxylate
Properties: colorless, crystalline substance, melting point 49°–54° C.

Example E7)

Ethyl 1-butyl-5-chloroindole-2-carboxylate
Properties: oil.

Example E8)

Ethyl 5-benzyloxy-1-methylindole-2-carboxylate
Properties: colorless, crystalline substance, melting point 120°–127° C.

Example E9)

Ethyl 5-fluoro-1-methylindole-2-carboxylate
Properties: colorless, crystalline substance, melting point 68°–69° C.

Example E10

Ethyl 5-chloro-1-(4-picolyl)indole-2-carboxylate
Properties: melting point 76°–78° C.

F. Hydrolysis of indole-2-carboxylic acid esters is carried out, for example, by heating the indole-2-carboxylic acid ester in a mixture of water and methanol with about 3 mol of NaOH until the suspension has dissolved. Working up, after rendering acid to pH 1 to 2 with 2N hydrochloric acid and extraction or crystallization.

Example F1)

5-Chloro-1-methylindole-2-carboxylic acid
Properties: decomposition at 235°–239° C.

Example F2)

1-(2-Dimethylaminoethyl)indole-2-carboxylic acid;
Note: isolation by crystallization from a little water as the inner salt at pH 4–5.
Properties: colorless, crystalline substance, melting point 214°–216° C.

Example F3)

1-(3,4-Dichlorobenzyl)indole-2-carboxylic acid
Properties: colorless, crystalline solid; melting point 152°–155° C.

Example F4)

5-Chloro-1-ethylindole-2-carboxylic acid
Properties: colorless, crystalline solid; melting point 194°–200° C.

Example F5)

5-Chloro-1-propylindole-2-carboxylic acid
Properties: colorless, crystalline solid; melting point 152°–154° C.

Example F6)

1-Butyl-5-chloroindole-2-carboxylic acid
Properties: colorless, crystalline solid; melting point 175° C.

Example F7)

5-Benzyloxy-1-methylindole-2-carboxylic acid
Properties: colorless, crystalline solid; melting point 218°–222° C.

Example F8)

5-Fluoro-1-methylindole-2-carboxylic acid
Properties: colorless, crystalline solid; melting point 227° C.

Example F9)

3,5-Dichloroindole-2-carboxylic acid
Properties: colorless, crystalline solid; melting point 235°–2400C.

Example F10)

3,5-Dichloro-1-methylindole-2-carboxylic acid
Properties: colorless, crystalline solid; melting point 250°–252° C.

Example F11)

3,5-Dichloro-1-(2-dimethylaminoethyl)indole-2-carboxylic acid
Properties: colorless, crystalline solid; melting point 243°–246° C.

Example F12

5-Methoxy-1-methylindole-2-carboxylic acid
Properties: colorless, crystalline solid; melting point 211°–214° C.

Example F13

3,5-Dichloro-1-(4-picolyl)indole-2-carboxylic acid
Properties: colorless, crystalline solid; melting point 228°–232° C.

Example F14

5-Chloro-1-(4-picolyl)indole-2-carboxylic acid
Properties: melting point 288°–290° C.

Example F15

3-Chloro-5-fluoro-1-methylindole-2-carboxylic acid
Properties: colorless, crystalline solid; melting point 222°–225° C.

Example F16

3-Isopropyl-5-methoxyindole-2-carboxylic acid, crystalline solid; melting point 156°–158° C.

Example F17

5-Chloro-3-phenylsulfonyl-1-methylindole-2-carboxylic acid
Properties: colorless, crystalline solid; melting point 238°–241° C.

Example F18

3-iodoindole-2-carboxylic acid
Properties: colorless, crystalline solid; melting point 177°–179° C.

Example F19

3-Iodo-1-methylindole-2-carboxylic acid
Properties: colorless, crystalline solid; melting point 177°–179° C. (decomposition)

G. Preparation of alkanedione monophenylhydrazones

General synthesis instructions:

A solution of 0.127 mol of NaOH in 20 ml of water is added to a solution of 0.103 mol of β-ketocarboxylic acid ester in 25 ml of ethanol, while stirring, and the mixture is stirred at room temperature for 30 minutes. 200 ml of water are then added and the mixture is stirred at room temperature for a further 4 hours and extracted with about 50–100 ml of diethyl ether.

An ice-cold diazonium salt solution, which was prepared as follows, is poured into the aqueous phase thus prepared:

150 ml of 18% strength hydrochloric acid are added to 0.1 mol of the aniline component and the mixture is heated, a thick suspension of crystals usually forming. After cooling, a solution of 0.1 mol of sodium nitrite is added dropwise, while stirring thoroughly, under the surface of the liquid such that the temperature is kept between 0° and 5° C., and the mixture is subsequently stirred for a further 10 minutes after the addition. The resulting, usually largely clear solution of the diazonium salt is poured in portions into the alkaline solution of the β-ketocarboxylic acid ester. After addition of about 300 ml of water, the mixture is brought to pH 5 by introduction of sodium acetate and the crystalline precipitate is filtered, or oily precipitates are extracted with ethyl acetate.

Example G1)

Aniline: 4-chloroaniline, β-keto ester: ethyl 2-ethylacetoacetate

End product: 2,3-pentanedione 3-N-(4-chlorophenyl)hydrazone; melting point 153°–157° C.

Example G2)

Aniline: 4-chloroaniline, β-keto ester: ethyl 2-benzylacetoacetate

End product: 1-phenylbutane-2,3-dione 3-N-(4-chlorophenyl)hydrazone; melting point 98°–104° C.

Example G3)

Aniline: 3,5-dichloroaniline, β-keto ester: ethyl 2-ethylacetoacetate

End product: 2,3-pentanedione 3-N-(3,5-dichlorophenyl)hydrazone; melting point 175° C.

Example G4)

Aniline: 2,4-dichloroaniline, β-keto ester: ethyl 2-ethylacetoacetate

End product: 2,3-pentanedione 3-N-(2,4-dichlorophenyl)hydrazone; melting point 48°–53° C.

Example G5)

Aniline: 2,3,4-trichloroaniline, β-keto ester: ethyl 2-ethylacetoacetate

End product: 2,3-pentanedione 3-N-(2,3,4-trichlorophenyl)hydrazone; melting point 214°–218° C.

Example G6)

Aniline: 4-isopropylaniline, β-keto ester: ethyl 2-ethylacetoacetate

End product: 2,3-pentanedione 3-N-(4-isopropylphenyl)hydrazone; melting point 214°–218° C.

Example G7)

Aniline: 4-Aminobenzophenone, β-keto ester: ethyl 2-ethylacetoacetate

End product: 2,3-pentanedione 3-N-(4-benzoylphenyl)hydrazone; melting point 114°–118° C.

Example G8)

Aniline: p-toluidine, β-keto ester: ethyl 2-ethylacetoacetate

End product: 2,3-pentanedione 3-N-(4-methylphenyl)hydrazone; melting point 136° C. (decomposition)

Example G9)

Aniline: 3,5-dimethylaniline, β-keto ester: ethyl 2-ethylacetoacetate

End product: 2,3-pentanedione 3-N-(3,5-dimethylphenyl)hydrazone; melting point 122° C. (decomposition)

Example G10)

Aniline: 4-trifluoromethylaniline, β-keto ester: ethyl 2-ethylacetoacetate

End product: 2,3-pentanedione 3-N-(4-trifluoromethylphenyl)hydrazone; melting point 120° C.

Example G11)

Aniline: 3,5-bis-trifluoromethyl-aniline, β-keto ester: ethyl 2-ethylacetoacetate End product: 2,3-pentanedione 3-N-(3,5-bis-trifluoromethylphenyl)hydrazone Melting point extends from 110° to 160° C.

Example G12)

Aniline: 4-cyclohexylaniline, β-keto ester: ethyl 2-ethylacetoacetate

End product: 2,3-pentanedione 3-N-(4-cyclohexylphenyl)hydrazone; melting point 107° C.

H. Preparation of 2-acetylindole derivatives by acid cyclization of phenylhydrazones (G.) (modified synthesis of Rajur et al., Synthetic Commun. (1992) 22: 421–428)

General synthesis instructions:

0.02 mol of a phenylhydrazone (see G) are dissolved in 70 ml of trifluoroacetic acid, a few drops of trifluoromethanesulfonic acid are added and the mixture is boiled under a reflux condenser for 5–10 hours, the progress of the reaction being monitored by thin layer chromatography. The solvent is distilled off, water is added to the usually dark residue and the crystalline precipitate is filtered off.

Example H1

2-Acetyl-5-chloro-3-methylindole; melting point 172°–176° C.

Example H2

2-Acetyl-5-chloro-3-phenylindole; melting point 124° C.

Example H3

2-Acetyl-4,6-dichloro-3-methylindole; melting point 178° C. (from a little ethanol)

Example H4

2-Acetyl-5,7-dichloro-3-methylindole; melting point 165°–168° C.

Example H5

2-Acetyl-4,5,6-trichloro-3-methylindole; long extended melting point 188°–202° C.

Example H6

2-Acetyl-5-isopropyl-3-methylindole; melting point 174°–177° C.

Example H7

2-Acetyl-5-benzoyl-3-methylindole; melting point 158°–164° C.

Example H8

2-Acetyl-3,5-dimethylindole was methylated in the 1-position without isolation

Example H9

2-Acetyl-3,4,6-trimethylindole; melting point from 156° C.

Example H10

2-Acetyl-5-trifluoromethyl-3-methylindole: melting point from 246° C.

Example H11

2-Acetyl-5-cyclohexyl-3-methylindole; melting point from 209°–212° C.

Example H12

2-Acetyl-5-trifluoromethyl-3-methylindole; melting point from 314° C.

I. Preparation of indole-2-carboxylic acid derivatives from 2-acetylindole derivatives General synthesis instructions:

12.5 g (0.079 mol) of bromine are slowly added dropwise to a solution of 12.5 g (0.314 mol) of sodium hydroxide in 120 ml of water, while maintaining a reaction temperature of between 0° and −5° C., and 100 ml of cooled dioxane (14° C.) are then added.

The solution is now slowly added dropwise to a cooled solution of 0.0242 mol of the 2-acetylindole such that the reaction temperature is kept between 10° and 15° C. The mixture is stirred at 15°–20° C. for a further 4 hours and a solution of 0.033 mol of sodium sulfite in 40 ml of water is then added. The reaction mixture is boiled under a reflux condenser for 30 minutes and, after cooling to about 60° C., about 30–40 ml of concentrated HCl are added. After cooling in an ice-bath, the crystals are filtered off.

Example I/1)

5-Chloro-1,3-dimethylindole-2-carboxylic acid, melting point 244°–247° C.

Example I/2)

5,7-Dichloro-1,3-dimethylindole-2-carboxylic acid, melting point 228°–232° C.

Example I/3)

4,6-Dichloro-1,3-dimethylindole-2-carboxylic acid, melting point 212° C.

Example I/4)

5-Chloro-1-methyl-3-phenylindole-2-carboxylic acid, melting point 218°–220° C.

Example I/5)

4,5,6-Trichloro-1,3-dimethylindole-2-carboxylic acid, melting point 232°–237° C. (decomposition)

Example I/6)

5-Benzoyl-1-methyl-1,3-dimethylindole-2-carboxylic acid, melting point 238°–240° C.

OTHER PRECURSORS

Other precursors 1:

Ethyl 3-isopropyl-5-methoxyindole-2-carboxylate 0.01 mol of 4-methoxyphenylhydrazine hydrochloride is reacted with ethyl 4-methyl-2-ketovalerate in boiling anhydrous ethanol (boiling time: 18 hours), the solvent is then evaporated off, water is then added, the mixture is extracted with ethyl acetate, the organic phase is washed with aqueous sodium chloride solution and dried and the solvent is distilled off.

Recrystallization from n-heptane. Colorless crystals, melting point 83°–90° C.

Other precursors 2: (Ullmann arylation on the indole):

A mixture of 0.015 mol of indole-2-carboxylic acid, 50 ml of anhydrous dimethylformamide, 0.0165 mol of bromobenzene, 0.5 g of Cu(II) oxide and 0.032 mol of KOH is boiled under a reflux condenser, while stirring under an argon atmosphere, for 5 hours. The dark suspension is poured into ice-water, the mixture is stirred for 30 minutes and filtered through a clarifying layer or a layer of active charcoal and the filtrate is treated with active charcoal again. After filtration and acidification to pH 1–2 with concentrated HCl, the desired acid is precipitated, filtered off, washed several times with water and dried.

Other precursors 2 a): 5-Methoxy-1-phenylindole-2-carboxylic acid; colorless crystals, melting point 194°–197° C.

Pharmacological data:

Inhibition of the $Na^+/H^+$ exchanger of rabbit erythrocytes

White New Zealand rabbits (Ivanovas) were given a standard diet with 2% of cholesterol for six weeks in order to activate the $Na^+/H^+$ exchange and thus to be able to determine the $Na^+$ influx into the erythrocytes via $Na^+/H^+$ exchange by flame photometry. The blood was taken from the ear arteries and rendered non-coagulable by 25 international units of potassium-heparin. A portion of each sample was used for duplicate determination of the hematocrit by centrifugation. Aliquots of in each case 100 µl were used for measurement of the $Na^+$ starting content of the erythrocytes.

To determine the amiloride-sensitive sodium influx, 100 µl of each blood sample were incubated at pH 7.4 and 37° C. in 5 ml portions of a hyperosmolar salt/sucrose medium (mmol/l: 140 NaCl, 3 KCl, 150 sucrose, 0.1 ouabain, 20 tris-hydroxymethylaminomethane). The erythrocytes were then washed three times with ice-cold $MgCl_2$/ouabain solution (mmol/l: 112 $MgCl_2$, 0.1 ouabain) and hemolyzed in 2.0 ml of distilled water. The intracellular sodium content was determined by flame photometry.

The net $Na^+$ influx was calculated from the difference between the sodium starting values and the sodium content of the erythrocytes after incubation. The sodium influx which can be inhibited by amiloride was obtained from the difference between the sodium content of the erythrocytes after incubation with and without amiloride $3 \times 10_{-4}$ mol/l. This procedure was also followed with the compounds according to the invention.

RESULTS

Inhibition of the $Na^+/H^+$ exchanger:

| Example | $IC_{50}$ mol/l |
|---------|-----------------|
| 52 | $4 \times 10^{-8}$ |
| 53 | $5 \times 10^{-8}$ |
| 54 | $2 \times 10^{-7}$ |
| 61 | $3 \times 10^{-7}$ |
| 69 | $5 \times 10^{-8}$ |
| 86 | $3 \times 10^{-8}$ |
| 104 | $2 \times 10^{-7}$ |
| 106 | $5 \times 10^{-8}$ |

We claim:

1. A benzo-fused heterocyclic compound having a 5-membered ring of the formula (I)

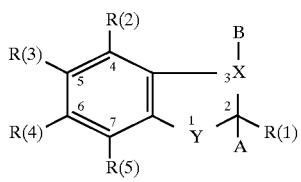

(I)

or a pharmaceutical tolerated salt thereof, in which:

X is CR(6);
Y is NR(7);
A and B
  together are a bond or are both hydrogen;
one of the substituents R(1) to R(6) is a —CO—N=C(NH$_2$)$_2$ group;
the other respective substituents R(1) to R(6) are independently hydrogen, F, Cl, Br, I or (C$_1$–C$_6$)-alkyl;
up to two of the other substituents R(1) to R(6) are independently CN, NO$_2$, N$_3$, (C$_1$–C$_4$)-alkoxy or CF$_3$;
up to one of the other substituents is R(8)—C$_n$H$_{2n}$—Z;
n is zero to 10;
  wherein the alkylene chain —C$_n$H$_{2n}$— is a straight-chain or is branched and
  wherein a carbon atom is optionally replaced by an oxygen atom, an S atom or an N atom;
R(8) is hydrogen, (C$_2$–C$_6$)-alkenyl or (C$_3$–C$_{10}$)-cycloalkyl, which is unsubstituted or substituted by 1 to 4 methyl groups or an OH group, or has an ethylene group —CH=CH—, and wherein a methylene group is optionally replaced by an oxygen atom, an S atom or an N atom;

or

R(8) is phenyl, which is unsubstituted or substituted by 1 to 3 substituents selected from the group consisting of F, Cl, Br, I, CF$_3$, CH$_3$—S(O)$_s$— and R(9)—W$_y$—;
s is zero, 1 or 2;
R(9) is H, methyl or ethyl;
W is oxygen or NR(10);
R(10) is H or methyl;
y is zero or 1;

or

R(8) is C$_m$F$_{2m+1}$;
m is 1 to 3;

or

R(8) is 1- or 2-naphthyl, pyridyl, quinolyl or isoquinolyl;
Z is —CO, CH$_2$— or [CR(11)(OH)]$_q$;
q is 1, 2 or 3;
R(11) is H or methyl;

or

Z is oxygen or —NR(12)—;
R(12) is H or methyl;

or

Z is —S(O)$_s$—;
s is zero, 1 or 2;

or

Z is —SO$_2$—NR(13)—;
R(13) is H or (C$_1$–C$_4$)-alkyl; and
R(7) is hydrogen, (C$_1$–C$_{10}$)-alkyl, (C$_2$–C$_{10}$)-alkenyl or R(8)—C$_n$H$_{2n}$—.

2. A compound of formula (I) as claimed in claim 1; in which x is CR(6);
Y is NR(7);
A and B
  together are a bond or are both hydrogen;
one of the substituents R(1) to R(6) is a —CO—N=C(NH$_2$)$_2$ group;
the other respective substituents R(1) to R(6) are independently hydrogen, F, Cl, Br, I or (C$_1$–C$_6$)-alkyl;
up to two of the other substituents R(1) to R(6) are independently CF$_3$ or (C$_1$–C$_4$) alkoxy;
up to one of the other substituents is CN, NO$_2$, N$_3$ or R(8)—C$_n$H$_{2n}$—Z;
n is zero to 4;
  wherein the alkylene chain —C$_n$H$_{2n}$— is a straight-chain or is branched and
  wherein a carbon atom is optionally replaced by an oxygen, an S atom or an N atom;
R(8) is hydrogen, (C$_2$–C$_6$)-alkenyl or (C$_3$–C$_{10}$)-cycloalkyl, which is unsubstituted or substituted by 1 to 2 methyl groups or an OH group, and wherein a methylene group is optionally replaced by an oxygen atom, an S atom or an N atom;

or

R(8) is phenyl, which is unsubstituted or substituted by 1 to 3 substituents selected from the group consisting of F, Cl, Br, I, CF$_3$, CH$_3$—S(O)$_s$— and R(9)—W$_y$—;
s is zero, 1 or 2;
R(9) is H, methyl or ethyl;
W is oxygen or NR(10);
R(10) is H or methyl;
y is zero or 1;

or

R(8) is C$_m$F$_{2m+1}$;
m is 1 to 3;

or

R(8) is pyridyl, quinolyl or isoquinolyl;
Z is —CO, —CH$_2$—, oxygen or —NR(12)—;
R(12) is H or methyl;

or

Z is —S(O)$_s$—;
S is zero, 1 or 2;

or

Z is —SO$_2$—NR(13)—;
R(13) is H or (C$_1$–C$_4$)-alkyl; and
R(7) is hydrogen, (C$_1$–C$_6$)-alkyl, (C$_2$–C$_4$)-alkenyl or R(8)—C$_n$H$_{2n}$—.

3. A compound of formula (I) as claimed in claim 1, in which

X is CR(6);
Y is NR(7);
A and B
  together are a bond or are both hydrogen;

R(1) is —CO—N=C(NH$_2$)$_2$;

the other respective substituents R(2) to R(6) are independently hydrogen, F, Cl, or Br;

up to two of the other substituents R(2) to R(6) are independently CF$_3$ or (C$_1$–C$_2$) alkoxy;

up to one of the other substituents R(2) to R(6) is R(8)—C$_n$H$_{2n}$—Z—;

n is zero, 1 or 2;

wherein the alkylene chain —C$_n$H$_{2n}$— is a straight-chain or is branched and wherein a carbon atom is optionally replaced by an oxygen atom, an S atom or an N atom;

R(8) is hydrogen or phenyl, which is unsubstituted or substituted by 1 to 3 substituents selected from the group consisting of F, Cl, CF$_3$, CH$_3$—S(O)$_s$— and R(9)—W$_y$—;

s is zero, 1 or 2;

R(9) is H or methyl;

W is oxygen;

y is zero or 1;

or

R(8) is pyridyl, quinolyl or isoquinolyl;

Z is —CO—, —CH$_2$—, S(O)$_s$— or oxygen;

s is zero, 1 or 2; and

R(7) is hydrogen, (C$_1$–C$_6$)-alkyl, (C$_2$–C$_4$)-alkenyl or R(8)—C$_n$H$_{2n}$—.

4. A compound as claimed in claim 1, said compound being:

5-chloro-1-methyl-2-indolylcarbonyl-guanidine hydrochloride, 5-chloro-1-ethyl-2-indolylcarbonyl-guanidine hydrochloride, 3-chloro-1-methyl-2-indolylcarbonyl-guanidine hydrochloride, 3,5-dichloro-1-methyl-2-indolylcarbonyl-guanidine hydrochloride, 5-fluoro-1-methyl-2-indolylcarbonyl-guanidine hydrochloride, 3-chloro-5-fluoro-1-methyl-2-indolylcarbonyl-guanidine hydrochloride, 4,6-dichloro-1,3-dimethyl-2-indolylcarbonyl-guanidine hydrochloride, 2-phenoxy-1-phenylindole-3-carboxylic acid guanidide methanesulfonic acid salt, 2-chloro-1-phenylindole-3-carboxylic acid guanidide methanesulfonic acid salt, 1-methylindoline-2-carboxylic acid guanidide hydrochloride, or 5-fluoro-1-methylindoline-2-carboxylic acid guanidide hydrochloride.

5. A compound of the formula (I) as claimed in claim 1, in which:

X is CR(6);

Y is NR(7);

A and B together are a bond;

or

A and B are both hydrogen;

one of the substituents R(1) to R(5) is —CO—N=C(NH$_2$)$_2$;

and the other respective substituents R(1) to R(5) are independently hydrogen, F, Cl, Br, I or (C$_1$–C$_6$)-alkyl;

or up to two of the other respective substituents R(1) to R(5) are independently CN, NO$_2$, N$_3$, (C$_1$–C$_4$)-alkyloxy or CF$_3$;

or up to one of the other respective substituents R(1) to R(5) is R(8)—C$_n$H$_{2n}$—Z—;

n is zero to 10;

wherein the alkylene chain —C$_n$H$_{2n}$— is a straight-chain or is branched and wherein a carbon atom is optionally replaced by an oxygen atom, an S atom or an N atom;

R(8) is hydrogen, (C$_2$–C$_6$)-alkenyl or (C$_3$–C$_{10}$)-cycloalkyl, which is unsubstituted or substituted by 1 to 4 methyl groups or an OH group, or has an ethylene group —CH=CH—, and wherein a methylene group is optionally replaced by an oxygen atom, an S atom or by an N atom;

or

R(8) is 1- or 2-naphthyl, pyridyl, quinolyl, isoquinolyl or phenyl, unsubstituted or substituted by 1 to 3 substituents selected from the group consisting of F, Cl, Br, I, CF$_3$, CH$_3$—S(O)$_s$— and R(9)—W$_y$—;

s is zero, 1 or 2;

R(9) is H, methyl or ethyl;

W is oxygen or NR(10);

R(10) is H or methyl;

y is zero or 1;

or

R(8) is C$_m$F$_{2m+1}$;

m is 1 to 3;

Z is —CO—, CH$_2$—, —[CR(11)(OH)]$_q$—, oxygen, —NR(12)—, —SOS$_s$— or —SO$_2$—NR(13)—;

q is 1, 2 or 3;

R(11) is H or methyl;

R(12) is H or methyl;

s is zero, 1 or 2;

R(13) is H or (C$_1$–C$_4$)-alkyl;

R(7) is hydrogen, (C$_1$–C$_{10}$)-alkyl, (C$_2$–C$_{10}$)-alkenyl or R(8)—C$_n$H$_{2n}$—;

n is zero, 1, 2, 3 or 4;

R(8) is NR(14)R(15) or CF$_3$;

R(14) and R(15) are hydrogen or methyl;

R(6) is defined as R(1) to R(5), but with the exception of hydrogen;

or

R(6) is also hydrogen, if one or two of the substituents R(1) to R(5) are CF$_3$;

or

R(6) is also hydrogen, if one of the substituents R(1) to R(5) is R(8)—C$_n$H$_{2n}$—Z—;

n is zero to 10;

wherein the alkylene chain —C$_n$H$_{2n}$— is a straight-chain or is branched and wherein a carbon atom is optionally replaced by an oxygen atom, an S atom or an N atom;

R(8) is hydrogen, (C$_2$–C$_6$)-alkenyl or (C$_3$–C$_{10}$)-cycloalkyl, which is unsubstituted or substituted by 1 to 4 methyl groups or an OH group, or has an ethylene group —CH=CH—, and wherein a methylene group is optionally replaced by an oxygen atom, an S atom or an N atom;

or

R(8) is 1- or 2-naphthyl, pyridyl, quinolyl, isoquinolyl or phenyl, unsubstituted or substituted by 1 to 3 substituents selected from the group consisting of F, Cl, Br, I, CF$_3$, CH$_3$—S(O)S— and R(9)—W$_y$—:

s is zero, 1 or 2;

R(9) is H, methyl or ethyl;

W is oxygen or NR(10);

R(10) is H or methyl;

y is zero or 1;

or

R(8) is $C_mF_{2m+1}$;

m is 1 to 3;

Z is CO, $[CR(11)OH]_q$, O, NR(12), $S(O)_s$ or $SO_2NR(13)$;

R(11) is H or methyl;

R(12) is H or methyl;

s is zero, 1 or 2;

q is 1, 2, or 3;

R(13) is H or $(C_1-C_4)$-alkyl;

or

R(6) is also hydrogen, if one of the substituents R(1) to R(5) is $R(8)$—$C_nH_{2n}$—Z—;

wherein a methylene group in the —$C_nH_{2n}$— group is replaced by an oxygen atom, an S atom or an N atom;

R(8) is hydrogen, $(C_2-C_6)$-alkenyl or $(C_3-C_{10})$-cycloalkyl, which is unsubstituted or substituted by 1 to 4 methyl groups or an OH group, or has an ethylene group —CH=CH—;

n is 1 to 10;

or

R(6) is also hydrogen, if one of the substituents R(1) to R(5) is $R(8)$—$C_nH_{2n}$—Z—;

n is zero;

R(8) is 1- or 2-naphthyl, pyridyl, quinolyl, isoquinolyl or phenyl, unsubstituted or substituted by 1 to 3 substituents selected from the group consisting of F, Cl, Br, I, $CF_3$, $CH_3$—S(O)S— and $R(9)$—$W_y$—;

s is zero, 1 or 2;

R(9) is H, methyl or ethyl;

W is oxygen or NR(10);

R(10) is H or methyl;

y is zero or 1;

Z is oxygen or NR(12);

R(12) is H or methyl;

or

R(6) is also hydrogen, if one of the substituents R(1) to R(5) is $R(8)C_nH_{2n}$—Z;

n is zero or 1;

R(8) is $C_mF_{2m+1}$;

m is 1 to 3;

Z is oxygen or NR(12); and

R(12) is H or methyl.

6. A compound of the formula (I) as claimed in claim 5, in which:

X is CR(6);

Y is NR(7);

A and B together are a bond;

or

A and B are both hydrogen;

one of the substituents R(1) to R(5) is —CO—N=C$(NH_2)_2$;

the other respective substituents R(1) to R(5) are independently hydrogen, F, Cl, Br, I or $(C_1-C_6)$-alkyl;

or up to two of the other respective substituents R(1) to R(5) are independently $(C_1-C_4)$-alkyloxy or $CF_3$;

or up to one of the other respective substituents R(1) to R(5) is CN, $NO_2$, $N_3$ or $R(8)$—$C_nH_{2n}$—Z—;

n is zero to 7;

wherein the alkylene chain —$C_nH_{2n}$— is a straight-chain or is branched and wherein a carbon atom is optionally replaced by an oxygen atom, an S atom or an N atom;

R(8) is hydrogen, $(C_3-C_6)$-alkenyl or $(C_5-C_8)$-cycloaklyl, which is unsubstituted or substituted by 1 or 2 methyl groups or an OH group, and wherein a methylene group is optionally replaced by an oxygen atom, an S atom or an N atom;

or

R(8) is pyridyl, quinolyl, isoquinolyl or phenyl, unsubstituted or substituted by 1 to 3 substituents selected from the group consisting of F, Cl, Br, I, $CF_3$, $CH_3$—$S(O)_s$— and $R(9)$—$W_y$—;

s is zero, 1 or 2;

R(9) is H, methyl or ethyl;

W is oxygen or NR(10);

R(10) is H or methyl;

y is zero or 1;

or

R(8) is $C_mF_{2m+1}$;

m is 1 to 3;

Z is —CO—, —$CH_2$—, oxygen, —NR(12)—, —$S(O)_s$— or —$SO_2$—NR(13)—;

R(12) is H or methyl;

s is zero, 1 or 2;

R(13) is H or $(C_1-C_4)$-alkyl;

R(6) is defined as R(1) to R(5), but with the exception of hydrogen;

or

R(6) is also hydrogen; if one or two of the substituents R(1) to R(5) are $CF_3$;

or

R(6) is also hydrogen, if one of the substituents R(1) to R(5) is $R(8)$—$C_nH_{2n}$—Z—;

n is zero to 4;

wherein the alkylene chain —$C_nH_{2n}$— is a straight-chain or is branched and wherein a carbon atom is optionally replaced by an oxygen atom, an S atom or an N atom;

R(8) is hydrogen, $(C_3-C_6)$-alkenyl or $(C_5-C_8)$-cycloalkyl, which is unsubstituted or substituted by 1 or 2 methyl groups or an OH group, and wherein a methylene group is optionally replaced by an oxygen atom, an S atom or an N atom;

or

R(8) is pyridyl, quinolyl or isoquinolyl or phenyl, unsubstituted or substituted by 1 to 3 substituents selected from the group consisting of F, Cl, Br, I, $CF_3$, $CH_3$—$S(O)_s$— and $R(9)$—$W_y$—;

s is zero, 1 or 2;

R(9) is H, methyl or ethyl;

W is oxygen or NR(10);

R(10) is H or methyl;

y is zero or 1;

or

R(8) is $C_mF_{2m+1}$;

m is 1 to 3;

Z is CO, $S(O)_s$ or $SO_2NR(13)$;

or

R(6) is also hydrogen, if one of the substituents R(1) to R(5) is $R(8)$—$C_nH_{2n}$—Z—;

wherein a methylene group in the —$C_nH_{2n}$— group is replaced by an oxygen atom, an S atom or an N atom;

n is zero to 7;

R(8) is hydrogen, $(C_3-C_6)$-alkenyl or $(C_5-C_8)$-cycloalkyl, which is unsubstituted or substituted by 1 or 2 methyl groups or an OH group, and wherein a methylene group is optionally replaced by an oxygen atom, an S atom or an N atom;

or
- R(8) is pyridyl, quinolyl, isoquinolyl or phenyl, unsubstituted or substituted by 1 to 3 substituents selected from the group consisting of F, Cl, Br, I, $CF_3$, $CH_3$—$S(O)_s$— and $R(9)$—$W_y$—;
- s is zero, 1 or 2;
- R(9) is H, methyl or ethyl;
- W is oxygen or NR(10);
- R(10) is H or methyl;
- y is zero or 1;

or
- R(8) is $C_mF_{2m+1}$;
- m is 1 to 3;
- Z is O or NR(12); and
- R(7) is hydrogen, $(C_1-C_{10})$-alkyl, $(C_2-C_{10})$-alkenyl or $R(8)$—$C_nH_{2n}$—;
- n is zero, 1, 2, 3 or 4;
- R(8) is NR(14)R(15) or $CF_3$; and
- R(14) and R(15) are hydrogen or methyl.

7. A compound of the formula (I) as claimed in claim 6, in which:
- X is CR(6);
- Y is NR(7);
- A and B
  together are a bond;

or
- A and B
  are both hydrogen;
- R(1) is —CO—N=C(NH₂)₂;
- the other respective substituents R(2) to R(5) are independently hydrogen, F, Cl, or Br;
- or up to two of the other respective substituents R(2) to R(5) are independently $(C_1-C_2)$-alkyloxy or $CF_3$;
- or up to one of the other respective substituents R(2) to R(5) is $R(8)$—$C_nH_{2n}$—$Z$—;
- n is zero, 1 or 2;
  - wherein the alkylene chain —$C_nH_{2n}$— is a straight-chain or is branched;
- R(8) is hydrogen;

or
- R(8) is pyridyl, quinolyl, isoquinolyl or phenyl, unsubstituted or substituted by 1 or 3 substituents selected from the group consisting of F, Cl, $CF_3$, $CH_3$—$S(O)_s$— and $R(9)$—$W_y$—;
- s is zero or 2;
- R(9) is H or methyl;
- W is oxygen;
- y is zero or 1;
- Z is —CO—, —$CH_2$—, oxygen, or —$S(O)_s$—;
- s is zero or 2;
- R(6) is defined as R(1) to R(5), but with the exception of hydrogen;

or
- R(6) is also hydrogen, if one or two of the substituents R(1) to R(5) are $CF_3$;

or
- R(6) is also hydrogen, if one of the substituents R(1) to R(5) is $R(8)$—$C_nH_{2n}$—$Z$—;
- n is zero, 1 or 2;
- R(8) is hydrogen, or
- R(8) is pyridyl, quinolyl or isoquinolyl or phenyl, unsubstituted or substituted by 1 to 3 substituents selected from the group consisting of F, Cl, Br, I, $CF_3$, $CH_3$—$S(O)_s$— and $R(9)$—$W_y$—,
- s is zero, 1 or 2;
- R(9) is H or methyl;
- W is oxygen;
- y is zero or 1;
- Z is CO, $S(O)_s$ or $SO_2NR(13)$;

or
- R(6) is also hydrogen, if one of the substituents R(1) to R(5) is $R(8)$—$C_nH_{2n}$—$Z$—;
- n is zero, 1 or 2;
- R(8) is pyridyl, quinolyl, isoquinolyl or phenyl, unsubstituted or substituted by 1 to 3 substituents selected from the group consisting of F, Cl, Br, I, $CF_3$, $CH_3$—$S(O)_s$— and $R(9)$—$W_y$—;
- s is zero, 1 or 2;
- R(9) is H or methyl;
- W is oxygen;
- y is zero or 1;
- Z is O or NR(12); and
- R(7) is hydrogen, $(C_1-C_6)$-alkyl, $(C_3-C_4)$-alkenyl or $R(8)$—$C_nH_{2n}$—;
- n is zero, 1, 2, 3 or 4;
- R(8) is NR(14)R(15) or $CF_3$; and
- R(14) and R(15) are hydrogen or methyl.

8. A pharmaceutical composition for treating arrhythmias, which comprises an effective amount for said treatment of a compound of formula (I) as claimed in claim 1 together with a pharmaceutically acceptable carrier.

9. A method for treating arrhythmias, which comprises administering to a host in need of said treatment an effective amount of a compound of the formula (I) as claimed in claim 1.

10. A method for treating or prophylaxis of cardiac infarction, which comprises administering to a host in need of said treatment an effective amount of a compound of the formula (I) as claimed in claim 1.

11. A method for treating or prophylaxis of angina pectoris, which comprises administering to a host in need of said treatment an effective amount of a compound of the formula (I) as claimed in claim 1.

12. A method for treating or prophylaxis of ischemic heart conditions, which comprises administering to a host in need of said treatment an effective amount of a compound of the formula (I) as claimed in claim 1.

13. A method for treating or prophylaxis of ischemic conditions of the peripheral and central nervous systems and of apoplexy, which comprises administering to a host in need of said treatment an effective amount of a compound of the formula (I) as claimed in claim 1.

14. A method for treating or prophylaxis of ischemic conditions of the peripheral organs and limbs, which comprises administering to a host in need of said treatment an effective amount of a compound of the formula (I) as claimed in claim 1.

15. A method for treating shock conditions, which comprises administering to a host in need of said treatment an effective amount of a compound of the formula (I) as claimed in claim 1.

16. A method for protective treatment in surgical operations and organ transplantations, which comprises administering to a host in need of said treatment an effective amount of a compound of the formula (I) as claimed in claim 1.

17. A method for preserving and storing transplants for surgical procedures, which comprises treating said transplants with an effective amount of a compound of the formula (I) as claimed in claim 1.

18. A method for treating diseases in which cell proliferation is a direct or collateral cause, which comprises administering to a host in need of said treatment an effective amount of a compound of the formula (I) as claimed in claim 1.

19. A method as claimed in claim 18, wherein the disease is atherosclerosis, a late complication of diabetes, a fibrotic disorder or prostate hyperplasia.

20. A method as claimed in claim 19, wherein the fibrotic disorder is pulmonary fibrosis, fibrosis of the liver or fibrosis of the kidneys.

21. A pharmaceutical composition for treating cardiac infarction, angina pectoris, ischemic conditions of the heart, of the peripheral and central nervous systems, of the peripheral organs and limbs, of apoplexy and of conditions of shock, which comprises an effective amount for said treatment of a compound of formula (I) as claimed in claim 1 together with a pharmaceutically acceptable carrier.

* * * * *